(12) United States Patent
Loh et al.

(10) Patent No.: US 8,816,059 B2
(45) Date of Patent: Aug. 26, 2014

(54) METHOD FOR PREDICTING AND DETECTING TUMOR METASTASIS

(75) Inventors: Yoke-peng Loh, Bethesda, MD (US); Niamh X. Cawley, Bethesda, MD (US); Saravana Radha Krishna Murthy, Rockville, MD (US); Terence K. Lee, Hong Kong (HK)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/006,603

(22) Filed: Jan. 14, 2011

(65) Prior Publication Data

US 2011/0152355 A1 Jun. 23, 2011

Related U.S. Application Data

(63) Continuation-in-part of application No. PCT/US2009/050460, filed on Jul. 14, 2009.

(60) Provisional application No. 61/080,508, filed on Jul. 14, 2008, provisional application No. 61/161,568, filed on Mar. 19, 2009.

(51) Int. Cl.
*C07H 21/04* (2006.01)
(52) U.S. Cl.
USPC ........................ 536/24.5; 536/24.31; 536/24.1
(58) Field of Classification Search
None
See application file for complete search history.

(56) References Cited

U.S. PATENT DOCUMENTS

| | | | | |
|---|---|---|---|---|
| 6,248,527 | B1 * | 6/2001 | Chen et al. | 435/6.11 |
| 6,812,339 | B1 * | 11/2004 | Venter et al. | 536/24.31 |
| 7,037,695 | B2 * | 5/2006 | Hiebsch | 435/183 |
| 2004/0235011 | A1 * | 11/2004 | Cooper et al. | 435/6 |
| 2007/0083334 | A1 * | 4/2007 | Mintz et al. | 702/19 |

OTHER PUBLICATIONS

Du et al., "Key peptide processing enzymes are expressed by breast cancer cells," *Cancer Lett.*, 165 (2), 211-218 (2001).
He et al., "Identification of carboxypeptidase E and gamma-glutamyl hydrolase as biomarkers for pulmonary neuroendocrine tumors by cDNA microarray," *Hum. Pathol.*, 35 (10), 1196-1209 (2004).
Jung et al., "Structural characterization of the rat carboxypeptidase-E gene," *Mol. Endocrinol.*, 5 (9), 1257-1268 (1991).
Kim et al., "Comparative oncogenomics identifies NEDD9 as a melanoma metastasis gene," *Cell*, 125 (7), 1269-1281 (2006).
Manser et al., "Processing and secretion of human carboxypeptidase E by C6 glioma cells," *Biochem. J.*, 280 (Pt. 3), 695-701 (1991).
Murthy et al., "Carboxypeptidase E: elevated expression correlated with tumor growth and metastasis in pheochromocytomas and other cancers," *Cell. Mol. Neurobiol.*, 30 (8), 1377-1381 (2010).
Zhang et al., "Sorting of carboxypeptidase E to the regulated secretory pathway requires interaction of its transmembrane domain with lipid rafts," *Biochem. J.*, 369 (Pt. 3), 453-460 (2003).

* cited by examiner

*Primary Examiner* — Kimberly Chong
(74) *Attorney, Agent, or Firm* — Leydig, Voit & Mayer, Ltd.

(57) ABSTRACT

The invention provides a method of determining the prognosis of cancer in a subject. The method comprises (a) obtaining a sample from the subject, (b) analyzing the sample for the expression level of a carboxypeptidase E (CPE) splice variant, and (c) correlating the expression level in the sample with the prognosis of cancer in the subject. The invention further provides a method of diagnosing cancer, methods of treatment, kits for detecting mRNA expression of a CPE-ΔN, and inhibitors of CPE-ΔN and compositions thereof.

8 Claims, 11 Drawing Sheets

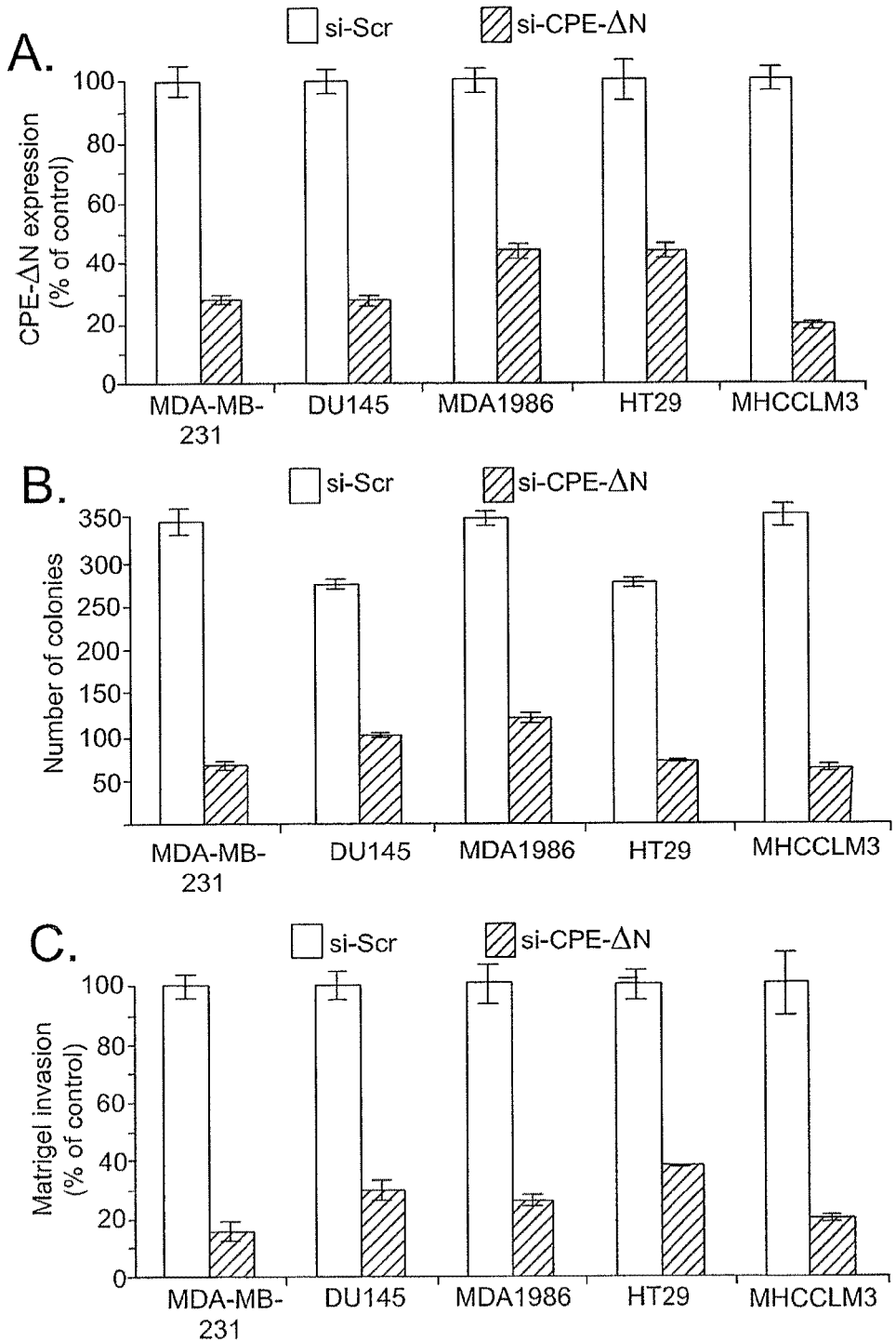

SEQUENCE LISTING

<160> NUMBER OF SEQ ID NOS: 27

<210> SEQ ID NO 1
<211> LENGTH: 2191
<212> TYPE: DNA
<213> ORGANISM: Homo sapiens

<400> SEQUENCE: 1

```
agtgcgcggg ctgacactca ttcagccggg gaaggtgagg cgagtagagg ctggtgcgga      60
acttgccgcc cccagcagcg ccggcgggct aagcccaggg ccgggcagac aaaagaggcc     120
gcccgcgtag gaaggcacgg ccggcggcgg cggagcgcag cgatggccgg gcatgaggcg     180
gcgccggcgg ctgcagcaag aggacggcat ctccttcgag taccaccgct accccgagct     240
gcgcgaggcg ctcgtgtccg tgtggctgca gtgcaccgcc atcagcagga tttacacggt     300
ggggcgcagc ttcgagggcc gggagctcct ggtcatcgag ctgtccgaca accctggcgt     360
ccatgagcct ggtgagcctg aatttaaata cattgggaat atgcatggga atgaggctgt     420
tggacgagaa ctgctcattt tcttggccca gtacctatgc aacgaatacc agaaggggaa     480
cgagacaatt gtcaacctga tccacagtac ccgcattcac atcatgcctt ccctgaaccc     540
agatggcttt gagaaggcag cgtctcagcc tggtgaactc aaggactggt tgtgggtcg     600
aagcaatgcc cagggaatag atctgaaccg gaactttcca gacctggata ggatagtgta     660
cgtgaatgag aaagaaggtg gtccaaataa tcatctgttg aaaaatatga agaaaattgt     720
ggatcaaaac acaaagcttg ctcctgagac caaggctgtc attcattgga ttatggatat     780
tccttttgtg ctttctgcca atctccatgg aggagacctt gtggccaatt atccatatga     840
tgagacgcgg agtggtagtg ctcacgaata cagctcctcc ccagatgacg ccattttcca     900
aagcttggcc cggcatact ctcctttcaa cccggccatg tctgacccca atcggccacc     960
atgtcgcaag aatgatgatg acagcagctt tgtagatgga accaccaacg gtggtgcttg    1020
gtacagcgta cctggaggga tgcaagactt caattacctt agcagcaact gttttgagat    1080
caccgtggag cttagctgtg agaagttccc acctgaagag actctgaaga cctactggga    1140
ggataacaaa aactccctca ttagctacct tgagcagata caccgaggag ttaaaggatt    1200
tgtccgagac cttcaaggta acccaattgc gaatgccacc atctccgtgg aaggaataga    1260
ccacgatgtt acatccgcaa aggatggtga ttactggaga ttgcttatac ctggaaacta    1320
taaacttaca gcctcagctc caggctatct ggcaataaca aagaaagtgg cagttcctta    1380
cagccctgct gctggggttg attttgaact ggagtcattt tctgaaagga agaagaggaa    1440
gaaggaagaa ttgatggaat ggtggaaaat gatgtcagaa actttaaatt tttaaaaagg    1500
cttctagtta gctgctttaa atctatctat ataatgtagt atgatgtaat gtggtctttt    1560
ttttagattt tgtgcagtta atacttaaca ttgattatt ttttaatcat ttaaatatta    1620
atcaactttc cttaaaataa atagcctctt aggtaaaaat ataagaactt gatatatttc    1680
attctcttat atagtattca ttttcctacc tatattacac aaaaaagtat agaaaagatt    1740
taagtaattt tgccatccta ggcttaaatg caatattcct ggtattattt acaatgcaga    1800
attttttgag taattctagc tttcaaaaat tagtgaagtt cttttactgt aattggtgac    1860
aatgtcacat aatgaatgct attgaaaagg ttaacagata cagctcggag ttgtgagcac    1920
tctactgcaa gacttaaata gttcagtata aattgtcgtt ttttttcttgt gctgactaac    1980
tataagcatg atcttgttaa tgcatttttg atgggaagaa aaggtacatg tttacaaaga    2040
ggttttatga aaagaataaa aattgacttc ttgcttgtac atataggagc aatactatta    2100
tattatgtag tccgttaaca ctacttaaaa gtttagggtt ttctcttggt tgtagagtgg    2160
cccagaattg cattctgaat gaataaaggt t                                    2191
```

<210> SEQ ID NO 2
<211> LENGTH: 440
<212> TYPE: PRT

<213> ORGANISM: Homo sapiens

<400> SEQUENCE: 2

```
Met Arg Arg Arg Arg Leu Gln Gln Glu Asp Gly Ile Ser Phe Glu
 1               5                  10                  15

Tyr His Arg Tyr Pro Glu Leu Arg Glu Ala Leu Val Ser Val Trp Leu
            20                  25                  30

Gln Cys Thr Ala Ile Ser Arg Ile Tyr Thr Val Gly Arg Ser Phe Glu
            35                  40                  45

Gly Arg Glu Leu Leu Val Ile Glu Leu Ser Asp Asn Pro Gly Val His
 50                  55                  60

Glu Pro Gly Glu Pro Glu Phe Lys Tyr Ile Gly Asn Met His Gly Asn
 65                  70                  75                  80

Glu Ala Val Gly Arg Glu Leu Leu Ile Phe Leu Ala Gln Tyr Leu Cys
                85                  90                  95

Asn Glu Tyr Gln Lys Gly Asn Glu Thr Ile Val Asn Leu Ile His Ser
                100                 105                 110

Thr Arg Ile His Ile Met Pro Ser Leu Asn Pro Asp Gly Phe Glu Lys
            115                 120                 125

Ala Ala Ser Gln Pro Gly Glu Leu Lys Asp Trp Phe Val Gly Arg Ser
130                 135                 140

Asn Ala Gln Gly Ile Asp Leu Asn Arg Asn Phe Pro Asp Leu Asp Arg
145                 150                 155                 160

Ile Val Tyr Val Asn Glu Lys Glu Gly Gly Pro Asn Asn His Leu Leu
                165                 170                 175

Lys Asn Met Lys Lys Ile Val Asp Gln Asn Thr Lys Leu Ala Pro Glu
            180                 185                 190

Thr Lys Ala Val Ile His Trp Ile Met Asp Ile Pro Phe Val Leu Ser
            195                 200                 205

Ala Asn Leu His Gly Gly Asp Leu Val Ala Asn Tyr Pro Tyr Asp Glu
210                 215                 220

Thr Arg Ser Gly Ser Ala His Glu Tyr Ser Ser Ser Pro Asp Asp Ala
225                 230                 235                 240

Ile Phe Gln Ser Leu Ala Arg Ala Tyr Ser Ser Phe Asn Pro Ala Met
                245                 250                 255

Ser Asp Pro Asn Arg Pro Pro Cys Arg Lys Asn Asp Asp Ser Ser
            260                 265                 270

Phe Val Asp Gly Thr Thr Asn Gly Gly Ala Trp Tyr Ser Val Pro Gly
            275                 280                 285

Gly Met Gln Asp Phe Asn Tyr Leu Ser Ser Asn Cys Phe Glu Ile Thr
290                 295                 300

Val Glu Leu Ser Cys Glu Lys Phe Pro Pro Glu Glu Thr Leu Lys Thr
305                 310                 315                 320

Tyr Trp Glu Asp Asn Lys Asn Ser Leu Ile Ser Tyr Leu Glu Gln Ile
            325                 330                 335

His Arg Gly Val Lys Gly Phe Val Arg Asp Leu Gln Gly Asn Pro Ile
            340                 345                 350

Ala Asn Ala Thr Ile Ser Val Glu Gly Ile Asp His Asp Val Thr Ser
            355                 360                 365

Ala Lys Asp Gly Asp Tyr Trp Arg Leu Leu Ile Pro Gly Asn Tyr Lys
370                 375                 380

Leu Thr Ala Ser Ala Pro Gly Tyr Leu Ala Ile Thr Lys Lys Val Ala
385                 390                 395                 400
```

| | | | | | | | | | | | | |
|---|---|---|---|---|---|---|---|---|---|---|---|---|
|Val|Pro|Tyr|Ser|Pro|Ala|Ala|Gly|Val|Asp|Phe|Glu|Leu|Glu|Ser|Phe|
| | | | |405| | | |410| | | |415|

| | | | | | | | | | | | | |
|---|---|---|---|---|---|---|---|---|---|---|---|---|
|Ser|Glu|Arg|Lys|Glu|Glu|Glu|Lys|Glu|Glu|Leu|Met|Glu|Trp|Trp|Lys|
| | | |420| | | |425| | | |430|

| | | | | | |
|---|---|---|---|---|---|
|Met|Met|Ser|Glu|Thr|Leu|Asn|Phe|
| | |435| | |440|

<210> SEQ ID NO 3
<211> LENGTH: 1949
<212> TYPE: DNA
<213> ORGANISM: Mus musculus

<400> SEQUENCE: 3

```
gtgaggcgag aggaggctgg tgctgagctc gccaactcca cccgggcccg ggcagacaaa      60
agaggccagc aagaggacgg catctccttc gagtaccacc gctatccaga gctgcgcgag     120
gcgctggtgt ccgtatggct gcagtgcacc gccatcagca gaatctacac agtggggcgc     180
agcttcgagg gccgggagct cctggtcatc gagctgtctg acaaccccgg ggtccatgag     240
ccgggtgaac ctgaatttaa atacattggg aacatgcatg gtaatgaggc ggttggacgg     300
gaactgctta ttttcttggc ccagtacctg tgtaacgagt accagaaagg caatgagaca     360
attgtcaacc tgatccacag cacccgaatt catatcatgc cctccttgaa ccccgacggc     420
tttgagaaag ccgcatcgca gcccggcgag ctgaaggact ggtttgtggg ccgcagcaac     480
gcccagggaa tagatctgaa ccgtaacttc ccagacctgg acaggatcgt gtatgttaat     540
gagaaagaag gcggtcctaa caatcacctg ctgaagaatc tgaagaaaat tgtggaccaa     600
aattcaaagc ttgcccccga gaccaaggct gtcattcact ggatcatgga cattccattt     660
gtgctttctg ccaatctgca cggaggagac cttgtggcta attacccata tgatgagaca     720
cggagcggta ctgctcacga atacagttcc tgccctgatg acgcaatttt ccaaagcttg     780
gctcgcgcgt actcttcttt caacccagtc atgtctgacc caatcgacc tcccctgtcgc    840
aagaatgacg atgacagcag cttttgtagat ggaacgacca atggtggtgc atggtacagc     900
gtccccggtg gaatgcaaga cttcaattac ctgagcagca actgcttcga gatcactgtg     960
gagcttagct gtgagaagtt cccaccggaa gagactctca aaagctactg gaagataac    1020
aaaaactccc tcatcagcta cctggagcag atacaccgag gtgttaaagg gtttgtccgt    1080
gaccttcagg gtaaccccgat tgccaacgca accatctctg tggacgggat agaccatgat    1140
gtcacctcgg ctaaggatgg ggattactgg cgattgcttg ctcctggaaa ctataaactt    1200
acagcctccg ctcctggcta cctggcaatc acaaagaaag tggcagttcc ttttagccct    1260
gctgttgggg tggactttga gcttgagtct ttctctgaaa ggaaggagga ggagaaggaa    1320
gaattgatgg agtggtggaa aatgatgtca gaaactttga attttttaaga aaggcttcta    1380
actaattgct ttaatctatc tatagactgt agtaagatgc aatgtggctc ttttcttta    1440
ggttgtgtgc agttgatatt taacattgat ttattttga tcatttaagt aatagttagt    1500
aatcacgtaa atacacccgg acagaaatat aatgtctgga tctacttcat tcttacatca    1560
acattcactt taaaatctat cgaagctctt ttaacgtaat gggtgacaat gtcacatgac    1620
agatgccatg aagaagtcaa ccgatatagc ttggatctgt gaaccctgta ctgcgagaat    1680
cacatagttc catataagtt gtccttagtc tcttgtgctg attcactgta taagcatgat    1740
cctggtaatg cactttggat gggaagaaaa tgtacgtgct tttcagaggg gctctgaaca    1800
gaatgaaaac ctagttcttg cgtgtacttt gaagaatgga attgtattag tcagcctgtt    1860
```

```
aatgccactt cagagtttgg ggttttgtct tgattgtaga ttggcccaga attgcattct    1920
gatgaataaa ggcaaaaaaa aaaaaaaaa                                      1949
```

<210> SEQ ID NO 4
<211> LENGTH: 364
<212> TYPE: PRT
<213> ORGANISM: Mus musculus

<400> SEQUENCE: 4

```
Met His Gly Asn Glu Ala Val Gly Arg Glu Leu Leu Ile Phe Leu Ala
1               5                   10                  15

Gln Tyr Leu Cys Asn Glu Tyr Gln Lys Gly Asn Glu Thr Ile Val Asn
            20                  25                  30

Leu Ile His Ser Thr Arg Ile His Ile Met Pro Ser Leu Asn Pro Asp
        35                  40                  45

Gly Phe Glu Lys Ala Ala Ser Gln Pro Gly Glu Leu Lys Asp Trp Phe
    50                  55                  60

Val Gly Arg Ser Asn Ala Gln Gly Ile Asp Leu Asn Arg Asn Phe Pro
65                  70                  75                  80

Asp Leu Asp Arg Ile Val Tyr Val Asn Glu Lys Glu Gly Gly Pro Asn
                85                  90                  95

Asn His Leu Leu Lys Asn Leu Lys Lys Ile Val Asp Gln Asn Ser Lys
            100                 105                 110

Leu Ala Pro Glu Thr Lys Ala Val Ile His Trp Ile Met Asp Ile Pro
        115                 120                 125

Phe Val Leu Ser Ala Asn Leu His Gly Gly Asp Leu Val Ala Asn Tyr
    130                 135                 140

Pro Tyr Asp Glu Thr Arg Ser Gly Thr Ala His Glu Tyr Ser Ser Cys
145                 150                 155                 160

Pro Asp Asp Ala Ile Phe Gln Ser Leu Ala Arg Ala Tyr Ser Ser Phe
                165                 170                 175

Asn Pro Val Met Ser Asp Pro Asn Arg Pro Pro Cys Arg Lys Asn Asp
            180                 185                 190

Asp Asp Ser Ser Phe Val Asp Gly Thr Thr Asn Gly Gly Ala Trp Tyr
        195                 200                 205

Ser Val Pro Gly Gly Met Gln Asp Phe Asn Tyr Leu Ser Ser Asn Cys
    210                 215                 220

Phe Glu Ile Thr Val Glu Leu Ser Cys Glu Lys Phe Pro Pro Glu Glu
225                 230                 235                 240

Thr Leu Lys Ser Tyr Trp Glu Asp Asn Lys Asn Ser Leu Ile Ser Tyr
                245                 250                 255

Leu Glu Gln Ile His Arg Gly Val Lys Gly Phe Val Arg Asp Leu Gln
            260                 265                 270

Gly Asn Pro Ile Ala Asn Ala Thr Ile Ser Val Asp Gly Ile Asp His
        275                 280                 285

Asp Val Thr Ser Ala Lys Asp Gly Asp Tyr Trp Arg Leu Leu Ala Pro
    290                 295                 300

Gly Asn Tyr Lys Leu Thr Ala Ser Ala Pro Gly Tyr Leu Ala Ile Thr
305                 310                 315                 320

Lys Lys Val Ala Val Pro Phe Ser Pro Ala Val Gly Val Asp Phe Glu
                325                 330                 335

Leu Glu Ser Phe Ser Glu Arg Lys Glu Glu Lys Glu Glu Leu Met
            340                 345                 350

Glu Trp Trp Lys Met Met Ser Glu Thr Leu Asn Phe
```

```
<210> SEQ ID NO 5
<211> LENGTH: 20
<212> TYPE: DNA
<213> ORGANISM: Homo sapiens

<400> SEQUENCE: 5
atggccgggc atgaggcggc                                               20

<210> SEQ ID NO 6
<211> LENGTH: 20
<212> TYPE: DNA
<213> ORGANISM: Homo sapiens

<400> SEQUENCE: 6
gctgcgcccc accgtgtaaa                                               20

<210> SEQ ID NO 7
<211> LENGTH: 39
<212> TYPE: DNA
<213> ORGANISM: Homo sapiens

<400> SEQUENCE: 7
gagcgcagcg atggccgggc atgaggcggc gccggcggc                          39

<210> SEQ ID NO 8
<211> LENGTH: 40
<212> TYPE: DNA
<213> ORGANISM: Homo sapiens

<400> SEQUENCE: 8
ggccctcgaa gctgcgcccc accgtgtaaa tcctgctgat                         40

<210> SEQ ID NO 9
<211> LENGTH: 9
<212> TYPE: DNA
<213> ORGANISM: Homo sapiens

<400> SEQUENCE: 9 cgggcatga                                                            9

<210> SEQ ID NO 10
<211> LENGTH: 9
<212> TYPE: DNA
<213> ORGANISM: Homo sapiens

<400> SEQUENCE: 10 ccccaccgt                                                            9

<210> SEQ ID NO 11
<211> LENGTH: 20
<212> TYPE: DNA
<213> ORGANISM: Homo sapiens

<400> SEQUENCE: 11
ccatctccgt ggaaggaata                                               20

<210> SEQ ID NO 12
<211> LENGTH: 20
<212> TYPE: DNA
<213> ORGANISM: Homo sapiens

<400> SEQUENCE: 12
```
cctggagctg aggctgtaag                                          20

<210> SEQ ID NO 13
<211> LENGTH: 40
<212> TYPE: DNA
<213> ORGANISM: Homo sapiens

<400> SEQUENCE: 13
gcgaatgcca ccatctccgt ggaaggaata gaccacgatg                    40

<210> SEQ ID NO 14
<211> LENGTH: 40
<212> TYPE: DNA
<213> ORGANISM: Homo sapiens

<400> SEQUENCE: 14
tgccagatag cctggagctg aggctgtaag tttatagttt                    40

<210> SEQ ID NO 15
<211> LENGTH: 10
<212> TYPE: DNA
<213> ORGANISM: Homo sapiens

<400> SEQUENCE: 15
tccgtggaag                                                     10

<210> SEQ ID NO 16
<211> LENGTH: 10
<212> TYPE: DNA
<213> ORGANISM: Homo sapiens

<400> SEQUENCE: 16
tccgtggaag                                                     10

<210> SEQ ID NO 17
<211> LENGTH: 20
<212> TYPE: DNA
<213> ORGANISM: Mus musculus

<400> SEQUENCE: 17
gacaaaagag gccagcaaga                                          20

<210> SEQ ID NO 18
<211> LENGTH: 18
<212> TYPE: DNA
<213> ORGANISM: Mus musculus

<400> SEQUENCE: 18
caggttcacc cggctcat                                            18

<210> SEQ ID NO 19
<211> LENGTH: 30
<212> TYPE: DNA
<213> ORGANISM: Mus musculus

<400> SEQUENCE: 19
cagacaaaag aggccagcaa gaggacggca                               30

<210> SEQ ID NO 20
<211> LENGTH: 29
<212> TYPE: DNA
<213> ORGANISM: Mus musculus

<400> SEQUENCE: 20
attcaggttc acccggctca tggaccccg                                              29

<210> SEQ ID NO 21
<211> LENGTH: 10
<212> TYPE: DNA
<213> ORGANISM: Mus musculus

<400> SEQUENCE: 21
aggccagcaa                                                                   10

<210> SEQ ID NO 22
<211> LENGTH: 10
<212> TYPE: DNA
<213> ORGANISM: Mus musculus

<400> SEQUENCE: 22
gttcacccgg                                                                   10

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
ctcttagctg agtgtcccgc                                                        20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
ctgatcgtct tcgaacctcc                                                        20

<210> SEQ ID NO 25
<211> LENGTH: 58
<212> TYPE: DNA
<213> ORGANISM: Homo sapiens

<400> SEQUENCE: 25
ccggccagta cctatgcaac gaatactcga gtattcgttg cataggtact ggtttttg              58

<210> SEQ ID NO 26
<211> LENGTH: 58
<212> TYPE: DNA
<213> ORGANISM: Homo sapiens

<400> SEQUENCE: 26
ccggctccag gctatctggc aataactcga gttattgcca gatagcctgg agtttttg              58

<210> SEQ ID NO 27
<211> LENGTH: 58
<212> TYPE: DNA
<213> ORGANISM: Homo sapiens

<400> SEQUENCE: 27
ccgggatagg atagtgtacg tgaatctcga gattcacgta cactatccta tcttttg               58

METHOD FOR PREDICTING AND DETECTING TUMOR METASTASIS

CROSS-REFERENCE TO RELATED APPLICATIONS

This patent application is a continuation-in-part of International Patent Application No. PCT/US09/50460, filed on Jul. 14, 2009, which claims the benefit of U.S. Provisional Patent Application No. 61/080,508, filed Jul. 14, 2008, and U.S. Provisional Patent Application No. 61/161,568, filed Mar. 19, 2009, which are each incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 16,441 Byte ASCII (Text) file named "707409ST25.TXT," created on Jan. 6, 2011.

BACKGROUND OF THE INVENTION

Detecting cancer prior to metastasis greatly increases the efficacy of treatment and the chances of a subject's long-term survival. Although biomarkers have been reported as useful in identifying aggressive tumor types and predicting prognosis (He, *Hum. Pathol.*, 35: 1196-209 (2004); and Brouwers, *Ann. N.Y. Acad. Sci.*, 1073: 541-56 (2006)), each biomarker is specific for a particular type of cancer. In addition, due to a lack of reliability, several markers typically are required to determine the prognosis and course of therapy.

There exists a desire in the art for a universal biomarker that can determine the prognosis for a number of different cancers.

BRIEF SUMMARY OF THE INVENTION

The invention provides a method of determining the prognosis of cancer in a subject. The method comprises (a) obtaining a sample from the subject, (b) analyzing the sample for an expression level of a carboxypeptidase E (CPE) splice variant that lacks the N terminus (CPE-ΔN), and (c) correlating the expression level of CPE-ΔN in the sample with the prognosis of cancer in the subject.

The invention provides a method of diagnosing cancer in a subject, the method comprising (a) obtaining a sample from the subject, (b) analyzing the sample for an expression level of a carboxypeptidase E (CPE) splice variant that lacks the N terminus (CPE-ΔN), and (c) correlating the expression level of CPE-ΔN in the sample to a diagnosis of cancer in the subject.

The invention also provides a method of treating a cancer in a subject by administering an effective amount of an inhibitor of CPE-ΔN.

The invention additionally provides a composition comprising an inhibitor of CPE-ΔN and a pharmaceutically acceptable carrier. In particular, the invention provides a nucleic acid comprising a nucleic acid sequence selected from the group consisting of SEQ ID NO: 25, SEQ ID NO: 26, and SEQ ID NO: 27.

The invention provides a kit for detecting mRNA expression of CPE-ΔN comprising one or more primers that detect CPE-ΔN mRNA.

BRIEF DESCRIPTION OF THE SEVERAL VIEWS OF THE DRAWING(S)

FIGS. 1 A-E are bar graphs depicting expression levels of hCPE-ΔN and NEDD9 (Neural precursor cell expressed, developmentally down-regulated gene 9) for HCC (A), prostate (B), breast (C), colon (D), and head and neck (H&N) (E) cancer cell lines, corrected for actin levels and expressed as mean±SEM in arbitrary units (n=3 separate experiments). The HCC cell lines represented are H2P (1), H2M (2), MHCC97L (3), MHCC97H (4), and MHCCLM3 (5). The prostate cancer cell lines represented are LNCAP (6), PC-3 (7), and DU145 (8). The breast cancer cell lines represented are MCF-7 (9), T47D (10), and MDA-MB-231 (11). The colorectal cell lines represented are SW480 (12), HT-116 (13), and HT-29 (14). The H&N cancer cell lines represented are TU167 (15), TU159 (16), and MDA-1986 (17). * indicates highly metastatic or aggressive cell lines.

FIGS. 2A-B are bar graphs depicting the fold increase of proliferation (A) or invasion (B) in MHCCLM3 cells transfected with CPE-ΔN or empty vector (EV). The data demonstrate increased proliferation (1.92±0.05 fold, SEM, n=3, p<0.0001) and invasion (2.72±0.15 fold, SEM, n=5, p=0.0013) in cells transfected with CPE-ΔN versus EV.

FIG. 3A is a bar graph depicting the CPE expression level (as a percent of control). Data is from Western blots of CPE-ΔN performed on highly metastatic tumor cell lines from breast (MDA-MB-231), prostate (DU145), head and neck (MDA1986), colorectal (HT-29), and liver (MHCCLM3) cancers transfected with si-scr (control) or si-CPE-ΔN (which suppresses CPE-ΔN and CPE mRNA expression). In particular, the bar graph shows the percent of ~40 kD CPE-ΔN in si-CPE-ΔN treated cells relative to si-scr treated cells (made equal to 100%). Mean values±SEM (n=3) are shown.

FIG. 3B is a bar graph depicting the number of colonies with >50 cells in si-scr treated cells and si-CPE-ΔN treated cells. Mean values±SEM (n=3) are shown.

FIG. 3C is a bar graph depicting the percent invasion of si-CPE-ΔN treated cells relative to the si-scr treated cells (made equal to 100%). Mean values±SEM (n=3) are shown.

Figure 4:
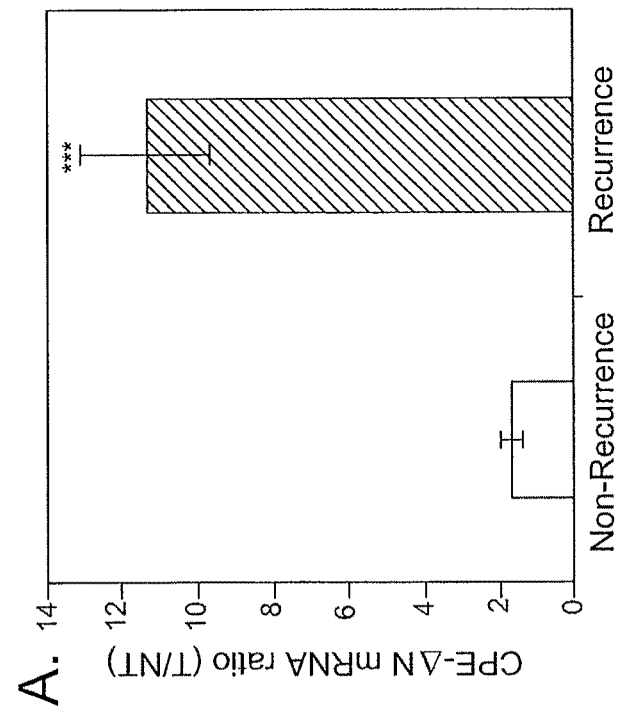
FIG. 4A is a bar graph depicting the ratio of hCPE-ΔN mRNA levels in tumor (T) versus surrounding non-tumor tissue (N) in HCC clinical samples for HCC patients that (i) were disease-free (Non-Recurrence; n=49) or (ii) had a recurrence of either intrahepatic or extrahepatic metastases one year after surgical resection (Recurrence; n=50). Mean±SEM (p<0.001) are shown.

FIG. 4B is a bar graph depicting the ratio of hCPE-ΔN protein levels in tumor (T) versus surrounding non-tumor tissue (N) in HCC clinical samples for HCC patients that (i) were disease-free (Non-Recurrence; n=34) or (ii) had a recurrence of either intrahepatic or extrahepatic metastases one year after surgical resection (Recurrence; n=46). The intensity of the CPE-ΔN band from the Western blots was quantified by densitometry and expressed in arbitrary units after correction for the actin level in the sample. Mean±SEM (p<0.001) are shown.

Figure 5:
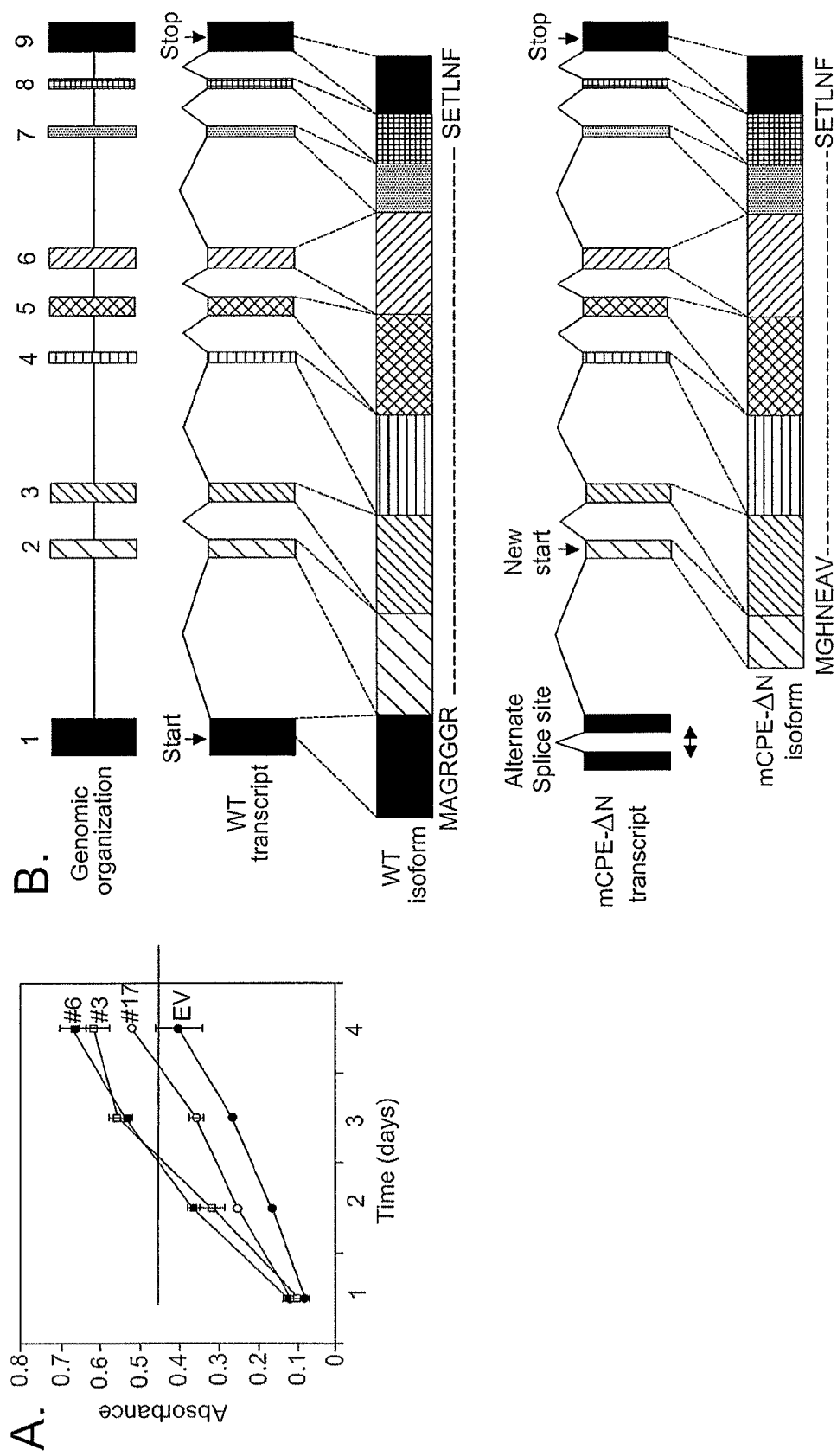

FIG. 5A is a growth curve for wild-type Neuro2A cells transfected with empty vector (EV) and clones stably expressing CPE (clones 3, 6, and 17). Each value represents means of replicates of 3±SEM. Experiments were repeated four times.

FIG. 5B is a diagram showing mouse wild-type (WT) and mouse CPE-ΔN mRNA and protein.

Figure 6:
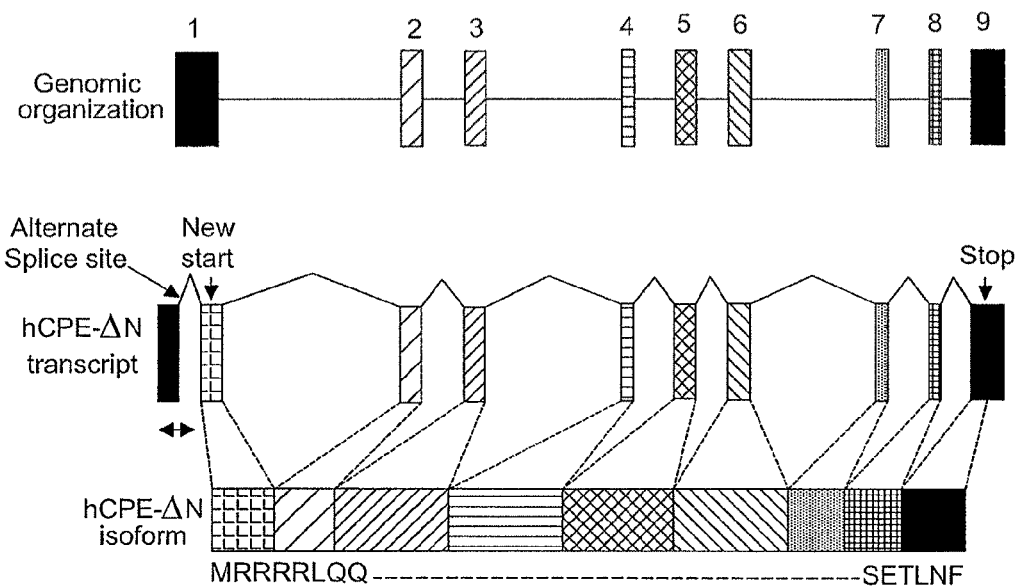
Figure 7A:
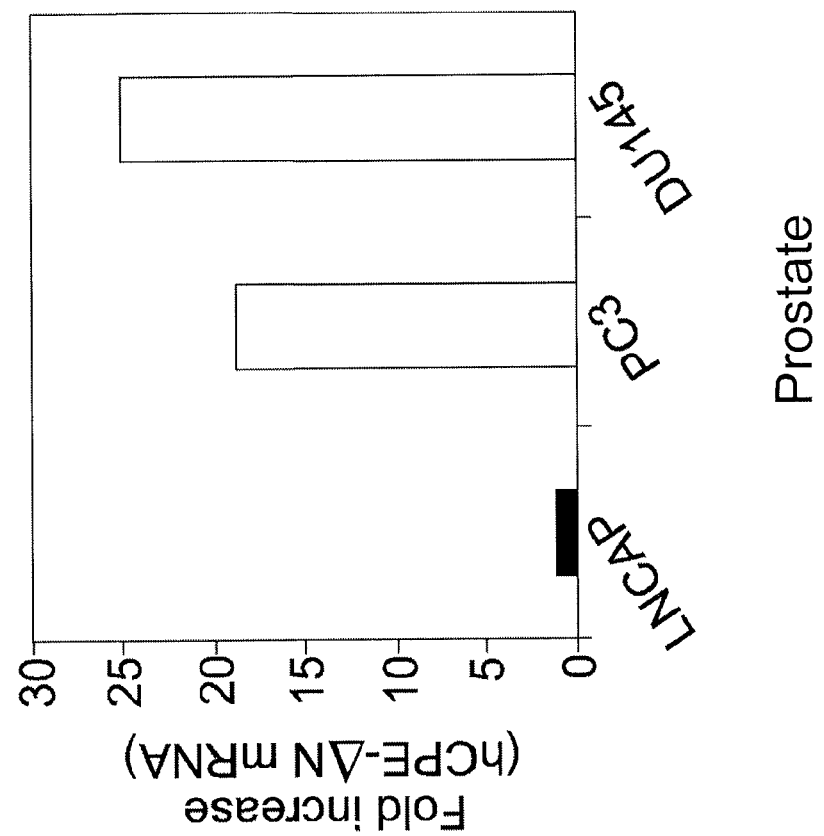
Figure 7B:
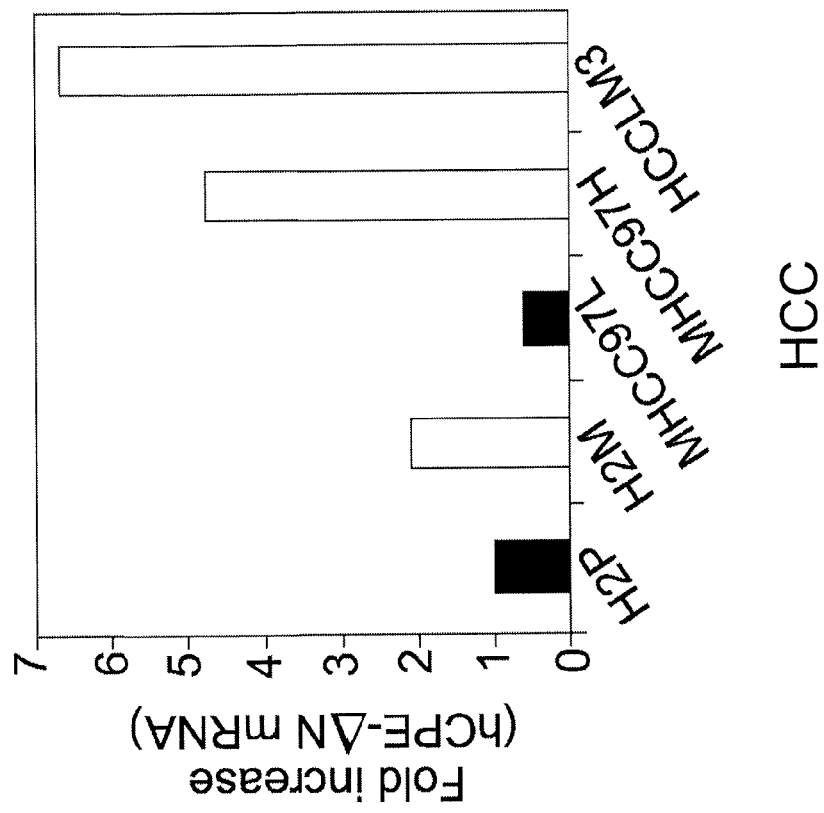
Figure 7D:
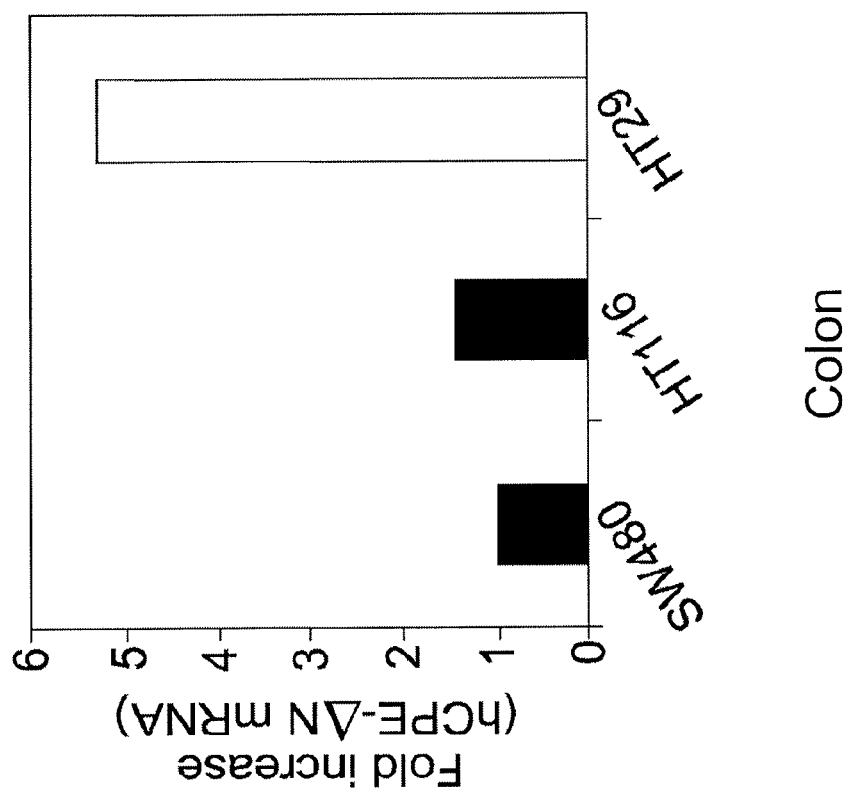
Figure 7C:
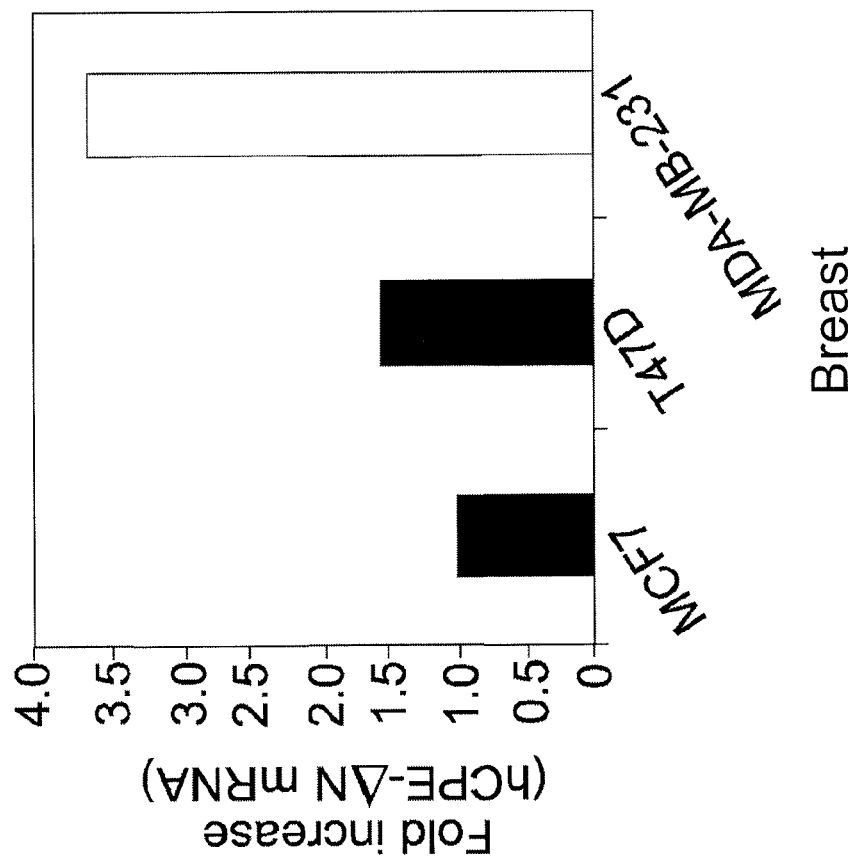
Figure 7E:
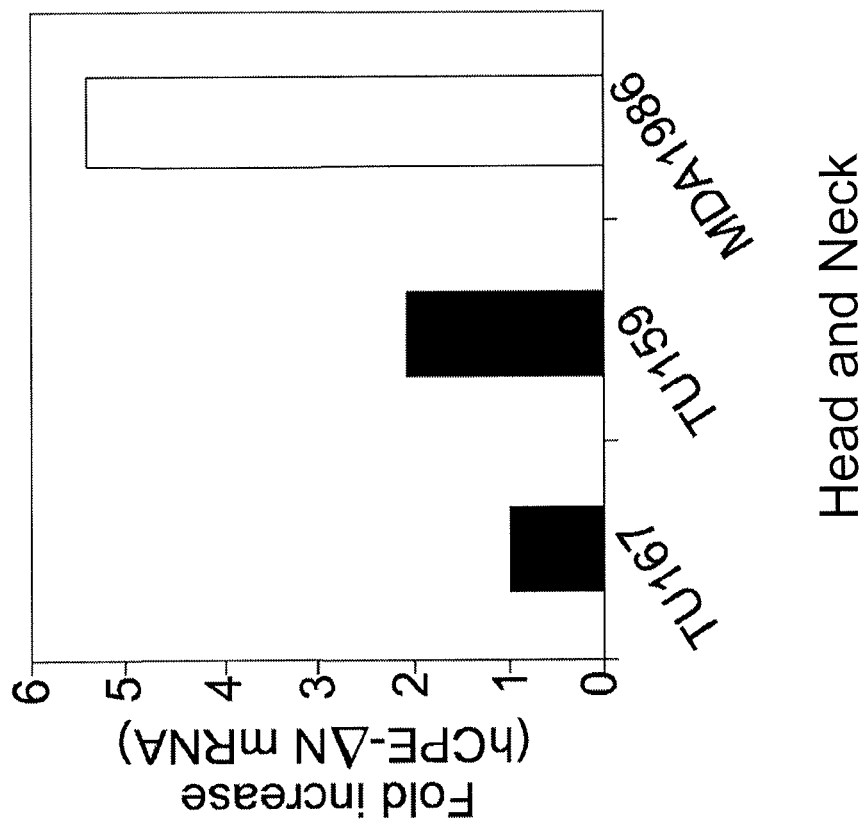

FIG. 6 is a diagram showing human WT and human CPE-ΔN mRNA and protein.

FIG. 7A-E are bar graphs depicting fold differences in expression of hCPE-ΔN mRNA in tumor cell lines relative to primary tumor cells with lowest hCPE-ΔN mRNA expression (first gray bar in each graph) made equal to 1. Highly metastatic cell lines: white bars, low metastatic cell lines: gray bars. The tumor cell lines represented are HCC (A), prostate (B), breast (C), colon (D), and head and neck (E).

DETAILED DESCRIPTION OF THE INVENTION

The inventors identified a splice variant isoform of the prohormone processing enzyme, carboxypeptidase E (CPE), which promotes growth and metastasis of several types of human epithelial-derived tumor cells. The splice variant isoform of CPE (CPE-ΔN) lacks the N-terminus (see FIG. 5B). In humans, the CPE-ΔN polypeptide comprises the amino acid sequence of SEQ ID NO: 2 and is encoded by the nucleic acid sequence of SEQ ID NO: 1. In mice, the CPE-ΔN polypeptide comprises the amino acid sequence of SEQ ID NO: 4 and is encoded by the nucleic acid sequence of SEQ ID NO: 3.

The invention provides a method of determining the prognosis of cancer in a subject. The invention provides a method of determining the prognosis of cancer in a subject. The method comprises (a) obtaining a sample from the subject, (b) analyzing the sample for an expression level of CPE-ΔN, and (c) correlating the expression level of CPE-ΔN in the sample with the prognosis of cancer in the subject.

The invention further provides a method of diagnosing cancer in a subject. The method comprises (a) obtaining a sample from the subject, (b) analyzing the sample for an expression level of CPE-ΔN (e.g., RNA or protein), and (c) correlating the expression level of CPE-ΔN in the sample with a diagnosis of cancer in the subject.

The sample to be analyzed can be any suitable tissue or fluid obtained from the subject. For example, the tissue can be tumor tissue, tissue adjacent to and/or surrounding the tumor, tissue from a location that is not adjacent to a primary tumor but that is suspected of harboring metastasized tumor, or blood.

The sample can be obtained by any suitable method. For example, sample tissue can be obtained via surgery, biopsy, resected tissue specimen, or arterial or venous blood withdrawal.

Preferably, the inventive methods further comprise the step of obtaining a sample from surrounding non-tumor tissue (N) for the purpose of comparison. In particular, the methods comprise (a) obtaining a sample from a tumor (T) and a sample from surrounding non-tumor tissue (N), (b) analyzing the tumor (T) sample for an expression level of CPE-ΔN (e.g., RNA or protein) relative to an expression level of CPE-ΔN in the surrounding non-tumor tissue sample (N), and (c) correlating the expression level of CPE-ΔN in tumor/non-tumor (T/N) with the prognosis of cancer in the subject.

The subject can be any mammal (e.g., mouse, rat, rabbit, hamster, guinea pig, cat, dog, pig, goat, cow, horse, primate, or human). Preferably, the subject is a human of any age and sex.

Without wishing to be bound by any particular theory, it is believed that CPE-ΔN promotes growth and metastasis of a variety of human cancer cells by up-regulating the expression of the metastasis gene, NEDD9 (see, e.g., Kim, Cell, 125: 1269-81(2006)). Additionally, it is believed that CPE-ΔN activates gene expression by epigenetic mechanisms by interacting with histone deacetylase and transcription factor SATB1. In this regard, CPE-ΔN can serve as a biomarker to reliably predict future metastasis of a variety of cancers based on the level of CPE-ΔN in the resected primary tumor.

Examples of cancers that can be detected utilizing the inventive method include nerve, adrenal, thyroid, liver (such as hepatocellular carcinoma (HCC)), prostate, lung, colorectal (e.g., colon, rectal), breast, head and neck, skin, pancreatic, ovarian, cervical, pheochromocytoma (PHEO)/paraganglioma (PGL) (e.g., PGL, PHEO), melanoma, esophagus, cervical, brain, and stomach cancer. The inventive method is particularly useful in detecting thyroid, PHEO/PGL, liver, prostate, colorectal, breast, and head and neck cancers.

The expression level of CPE-ΔN can be determined by detecting and, optionally, quantifying the levels of mRNA and/or protein of CPE-ΔN (referred to herein as "biomarker" or "biomarkers") in the sample.

Methods for detecting and quantifying such biomarkers are well within the art. In particular, suitable techniques for determining the presence and level of expression of the biomarkers in cells are within the skill in the art. According to one such method, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated herein by reference.

Methods for the preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the entire disclosures of which are incorporated herein by reference. For example, the nucleic acid probe can be labeled with, e.g., a radionuclide such as $^3$H, $^{32}$P, $^{33}$P, $^{14}$C, or $^{35}$S; a heavy metal; or a ligand capable of functioning as a specific binding pair member for a labeled ligand (e.g., biotin, avidin, or an antibody), a fluorescent molecule, a chemiluminescent molecule, an enzyme, or the like.

Probes can be labeled to high specific activity by either the nick translation method of Rigby et al., J. Mol. Biol., 113: 237-251 (1977), or by the random priming method of Fienberg, Anal. Biochem., 132: 6-13 (1983), the entire disclosures of which are herein incorporated by reference. The latter can be a method for synthesizing $^{32}$P-labeled probes of high specific activity from RNA templates. For example, by replacing preexisting nucleotides with highly radioactive nucleotides according to the nick translation method, it is possible to prepare $^{32}$P-labeled nucleic acid probes with a specific activity well in excess of $10^8$ cpm/microgram. Autoradiographic detection of hybridization then can be performed by exposing hybridized filters to photographic film. Densitometric scanning of the photographic films exposed by the hybridized filters provides an accurate measurement of biomarker levels. Using another approach, biomarker levels can be quantified by computerized imaging systems, such as the Molecular Dynamics 400-B 2D Phosphorimager (Amersham Biosciences, Piscataway, N.J., USA).

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA blotting hybridization techniques, determining the levels of RNA transcript can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. The inventive method encompasses automated quantification of CPE-ΔN (e.g., in formalin-fixed slides).

The relative number of RNA transcripts in cells also can be determined by reverse transcription of RNA transcripts, followed by amplification of the reverse-transcribed transcripts by polymerase chain reaction (RT-PCR). The levels of RNA transcripts can be quantified in comparison with an internal standard, for example, the level of mRNA from a standard gene present in the same sample. Suitable genes for use as an internal standard include, for example, myosin or glyceraldehyde-3-phosphate dehydrogenase (G3PDH). The methods for quantitative RT-PCR and variations thereof are within the skill in the art.

Any suitable primers can be used for the quantitative RT-PCR. Preferably, the primers are specific to CPE-ΔN and do not amplify wild-type CPE. It is within the skill in the art to generate primers specific to CPE-ΔN (see FIGS. 5B and 6 for a comparison of wild-type CPE and CPE-ΔN). Primers can be of any suitable length, but preferably are between 9 and 70 (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, as well as ranges of the values described herein) nucleotides.

In one embodiment, the invention provides a pair of primers specific to human CPE-ΔN, such as fwd: 5'-ATGGCCGGGCATGAGGCGGC-3' (SEQ ID NO: 5) and rev: 5'-GCTGCGCCCCACCGTGTAAA-3' (SEQ ID NO: 6). The primers also can have greater or fewer nucleotides. In particular, a maximum length primer pair specific to human CPE-ΔN is fwd: 5'-GAGCGCAGCGATGGCCGGGCATGAGGCGGCGCCGGCGGC-3' (SEQ ID NO: 7) and rev: 5'-GGCCCTCGAAGCTGCGCCCCACCGTGTAAATCCTGCTGAT-3' (SEQ ID NO: 8), and a minimal length primer pair specific to human CPE-ΔN is fwd: 5'-CGGGCATGA-3' (SEQ ID NO: 9) and rev: 5'-CCCCACCGT-3' (SEQ ID NO: 10). Primer pairs of intermediate lengths (e.g., between the minimal and maximum length primer pairs) also are encompassed by the invention.

In another embodiment, the invention provides a pair of primers specific to mouse CPE-ΔN, such as fwd: 5'-GACAAAAGAGGCCAGCAAGA-3' (SEQ ID NO: 17) and rev: 5'-CAGGTTCACCCGGCTCAT-3' (SEQ ID NO: 18). The primers also can have greater or fewer nucleotides. In particular, a maximum length primer pair specific to mouse CPE-ΔN is fwd: 5'-CAGACAAAAGAGGCCAGCAAGAGGACGGCA-3' (SEQ ID NO: 19) and rev: 5'-ATTCAGGTTCACCCGGCTCATGGACCCCG-3' (SEQ ID NO: 20), and a minimal length primer pair specific to mouse CPE-ΔN is fwd: 5'-AGGCCAGCAA-3' (SEQ ID NO: 21) and rev: 5'-GTTCACCCGG-3' (SEQ ID NO: 22). However, primer pairs of intermediate lengths (e.g., between the minimal and maximum length primer pairs) also are encompassed by the invention.

A tissue microarray can be utilized to detect biomarker expression. In the tissue microarray technique, a hollow needle is used to remove tissue cores as small as 0.6 mm in diameter from regions of interest in paraffin-embedded tissues such as clinical biopsies or tumor samples. These tissue cores are then inserted in a recipient paraffin block in a precisely spaced, array pattern. Sections from this block are cut using a microtome, mounted on a microscope slide and then analyzed by any method of standard histological analysis. Each microarray block can be cut into 100-500 sections, which can be subjected to independent tests. Tests commonly employed in tissue microarray include immunohistochemistry and fluorescent in situ hybridization.

In some instances, it may be desirable to use microchip technology to detect biomarker expression. The microchip can be fabricated by techniques known in the art. For example, probe oligonucleotides of an appropriate length, e.g., 40 nucleotides, are 5'-amine modified at position C6 and printed using commercially available microarray systems, e.g., the GENEMACHINE OmniGrid 100 Microarrayer and Amersham CODELINK activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6 times SSPE/30% formamide at 25° C. for 18 hours, followed by washing in 0.75 times TNT at 37° C. for 40 minutes. At positions on the array, where the immobilized probe DNA recognizes a complementary target cDNA in the sample, hybridization occurs. The labeled target cDNA marks the exact position on the array where binding occurs, thereby allowing automatic detection and quantification. The output consists of a list of hybridization events, which indicate the relative abundance of specific cDNA sequences, and therefore the relative abundance of the corresponding complementary biomarker, in the subject sample. According to one embodiment, the labeled cDNA oligomer is a biotin-labeled cDNA prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding biomarker in the subject sample.

The use of the array has one or more advantages for mRNA expression detection. First, the global expression of several hundred genes can be identified in a single sample at one time. Second, through careful design of the oligonucleotide probes, the expression of both mature and precursor molecules can be identified. Third, in comparison with Northern blot analysis, the chip requires a small amount of RNA and provides reproducible results using 2.5 μg of total RNA.

Protein in a sample can be detected using a variety of methods, such as protein immunostaining, immunoprecipitation, protein microarray, radio-immunoassay, and Western blot, all of which are well known in the art. Immunostaining is a general term in biochemistry that applies to any use of an antibody-based method to detect a specific protein in a sample. Similarly, immunoprecipitation is the technique of precipitating an antigen out of solution using an antibody specific to that antigen. This process can be used to enrich a given protein to some degree of purity. A Western blot is a method by which protein may be detected in a given sample of tissue homogenate or extract. It uses gel electrophoresis to separate denatured proteins by mass. The proteins are then transferred out of the gel and onto a membrane (typically nitrocellulose), where they are "probed" using antibodies specific to the protein. As a result, researchers can examine the amount of protein in a given sample and compare levels between several groups.

The expression level of CPE-ΔN can be correlated to a prognosis by comparing the biomarker expression level in the sample to biomarker expression in surrounding non-tumor tissue or to a standard. The standard with which the sample is compared can be a normalized standard and/or can be a sample taken at an earlier time from the same subject. That is, the sample can be compared to a sample taken from the same subject prior to treatment or the subject after treatment has commenced (i.e., the subject at an earlier time). In this way, the efficacy of treatment also can be determined.

The prognosis of the cancer in a subject can be determined in the inventive method. The cancer can be from a primary tumor and/or a metastatic lesion. In this regard, the prognosis can be that the cancer in the subject is or is not likely to metastasize or already has metastasized. The prognosis can be that the cancer in the subject is or is not a metastatic lesion. The prognosis also can include combinations of the above.

The diagnosis of cancer in a subject can be determined in the inventive method. Cancer cells are circulating in the blood even before a tumor is formed. After the tumor is formed, the tumor continually sheds cancer cells, which circulate in the blood. The expression level of CPE-ΔN in the sample can be used to determine whether a subject has cancer. For example, if the expression level of CPE-ΔN in a sample is >2 (e.g., 2.5, 3, 3.5, 4, 4.5, 5, 6, 7, 8, 9, 10, 20, 30, 40, 50, or greater) times than that of a control sample (e.g., a sample from a subject without cancer), the diagnosis is that the subject has cancer.

Additionally, the expression level of CPE-ΔN in a sample (e.g., blood sample) can be used to diagnose a suspected cancer as metastatic or having an increased risk of recurrence and future metastases. Even if a clinician diagnoses a cancer as benign based on the pathology of the primary tumor and the absence of visible metastases, a patient with increased expression of CPE-ΔN mRNA in the tumor has an increased risk of recurrence and future metastases (e.g., within 2, 3, 4, 5, 6, 7, 8, 9, or 10 years from resection of the primary tumor) based on the expression level of CPE-ΔN mRNA in the tumor. A patient with an increased expression of CPE-ΔN mRNA should be closely monitored for recurrence and metastases.

In one embodiment, the prognosis of cancer is based on the ratio of CPE-ΔN mRNA in tumor (T) versus non-tumor (NT) tissue. In particular, subjects with CPE-ΔN (e.g., mRNA or protein) T/NT ratios of <2 are much less likely than subjects with CPE-ΔN T/NT ratios of >2 (e.g., 2.5, 3, 3.5, 4, 4.5, 5, 6, 7, 8, 9, 10, 20, 30, 40, 50, or greater) to have metastatic cancer or a recurrence of cancer (e.g., metastatic cancer).

In another embodiment, the prognosis and/or diagnosis of cancer is based on the copy number of CPE-ΔN mRNA in tumor tissue. The copy number can be determined by any suitable method (e.g., quantitative RT-PCR).

When the cancer is pheochromocytoma (PHEO)/paraganglioma (PGL), CPE-ΔN mRNA copy numbers in tumor tissue of about 200,000 or less (e.g., 150,000 or less, 100,000 or less, or 50,000 or less) correlate to a prognosis that the tumor is benign. Patients in this group have a low risk of recurrence or metastasis (e.g., within 2, 3, 4, 5, 6, 7, 8, 9, or 10 years from resection of the primary tumor). In contrast, CPE-ΔN mRNA copy numbers in tumor tissue of about 1 million or greater (e.g., 2 million or greater, 3 million or greater, 4 million or greater, 5 million or greater, 6 million or greater, 7 million or greater, 8 million or greater, 9 million or greater, 10 million or greater, 15 million or greater, or 20 million or greater) correlate with a prognosis that the tumor is metastatic.

When the cancer is differentiated thyroid carcinoma (DTC), CPE-ΔN mRNA copy numbers in tumor tissue of about 200,000 or less (e.g., 150,000 or less, 100,000 or less, or 50,000 or less) correlate to a prognosis that the tumor is benign. CPE-ΔN mRNA copy numbers in tumor tissue of about 200,000 to about 600,000 (e.g., 250,000, 300,000, 350,000, 400,000, 450,000, 500,000, 550,000 or ranges of any of the values described herein) correlate to a low risk of recurrence or metastasis (e.g., within 2, 3, 4, 5, 6, 7, 8, 9, or 10 years from resection of the primary tumor). CPE-ΔN mRNA copy numbers in tumor tissue of about 600,000 to about 1 million (e.g., 650,000, 700,000, 750,00, 800,000, 850,000, 900,000, 950,000, or ranges of any of the values described herein) correlate to an increased risk of recurrence or metastasis (e.g., within 2, 3, 4, 5, 6, 7, 8, 9, or 10 years from resection of the primary tumor). CPE-ΔN mRNA copy numbers in tumor tissue of about 1 million or greater (e.g., 2 million or greater, 3 million or greater, 4 million or greater, 5 million or greater, 6 million or greater, 7 million or greater, 8 million or greater, 9 million or greater, 10 million or greater, or 15 million or greater) correlate with a prognosis that the tumor is metastatic.

The invention also provides a kit to measure CPE-ΔN mRNA and protein (e.g., from tissue biopsies and resected primary tumor tissues) for diagnostic or assay purposes. For example, the kit can comprise one or more primer pairs that detect CPE-ΔN mRNA levels and/or one or more probes that detect CPE-ΔN protein levels. Preferably, the primers and probes can differentiate between CPE-ΔN and wild-type CPE. The kits can be used to determine metastasis in a subject, to predict future recurrence/metastasis, and/or to monitor tumor progression in a subject (e.g., to determine efficacy of a cancer treatment).

The invention further provides a method of treatment for the subject that is accordance with the determined prognosis. The treatment can be any suitable treatment. Suitable treatments include chemotherapy, radiation, surgery, suppression of CPE-ΔN, NEDD9 inhibition, and combinations thereof. Methods of chemotherapy, radiation, and surgical intervention are well within the art and can be determined on a case-by-case basis depending on the location, type, and stage of the cancer.

In one embodiment, the treatment includes suppression of CPE-ΔN. In this regard, an effective amount of an inhibitor of CPE-ΔN is administered to the subject. Desirably, the inhibitor prevents metastasis or slows the progression of metastasis (e.g., by at least 5%, 10%, 15%, 20%, 25%, 30%, 35%, 40%, 50%, 55%, 60%, 65%, 70%, 75%, 80%, 85%, 90%, 95%, or 100%).

The inhibitor can be administered at any time following a prognosis determination. The inhibitor can be administered alone or in combination with other treatments. For instance, the inhibitor can be administered prior to surgical resection of a tumor. The inhibitor also can be administered following surgical resection of a tumor. One skilled in the art can readily determine an effective amount of the inhibitor composition to be administered to a given subject, by taking into account factors such as the size and weight of the subject, the extent of disease penetration, the age, health, and sex of the subject, the route of administration, and whether the administration is regional or systemic.

One skilled in the art also can readily determine an appropriate dosage regimen for administering a composition that alters biomarker levels or gene expression to a given subject. For example, the composition can be administered to the subject once (e.g. as a single injection or deposition). Alternatively, the composition can be administered multiple times on any suitable schedule, e.g., once or twice daily, monthly, bimonthly, or biannually. The administration of the treatment to a subject can be for a period ranging from days, weeks, months, or years. In certain embodiments, the treatment continues throughout the life of the subject. Where a dosage regimen comprises multiple administrations, it is understood that the effective amount of the composition administered to the subject can comprise the total amount of composition administered over the entire dosage regimen.

The inhibitor can be any suitable entity that suppresses/inhibits expression or transcriptional activity of CPE-ΔN. For example, the inhibitor can comprise a nucleic acid that is complementary to DNA or RNA (i.e., mRNA or tRNA) of CPE-ΔN that binds to and inhibits expression of CPE-ΔN. Alternatively, the treatment can include the administration of a NEDD9 inhibitor comprising a nucleic acid that is complementary to the NEDD9 DNA or RNA (i.e., mRNA or tRNA).

In this regard, the invention further provides a composition comprising an inhibitor of CPE-ΔN and/or a NEDD9 inhibitor and a pharmaceutically acceptable carrier.

Suitable compositions for inhibiting the expression of genes, such as the gene encoding CPE-ΔN and/or NEDD9, include double-stranded RNA (such as short- or small-interfering RNA or "siRNA"), antisense nucleic acids, and enzymatic RNA molecules such as ribozymes. These components can be targeted to a given biomarker gene product and can destroy or induce the destruction of the target biomarker gene product.

For example, expression of a given gene can be inhibited by inducing RNA interference of the gene with an isolated double-stranded RNA ("dsRNA") molecule which has at least 90%, for example, at least 95%, at least 98%, at least 99%, or 100%, sequence homology with at least a portion of the gene product. In a preferred embodiment, the dsRNA molecule is a "short or small interfering RNA" or "siRNA" (e.g., shRNA).

siRNA useful in the inventive methods comprise short double-stranded RNA from about 17 nucleotides to about 29 nucleotides in length, and preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target gene product.

As used herein, an siRNA "substantially identical" to a target sequence contained within the target nucleic sequence is a nucleic acid sequence that is identical to the target sequence or differs from the target sequence by at most one or two nucleotides. The sense and antisense strands of the siRNA can comprise two complementary, single-stranded RNA molecules, or can comprise a single molecule in which two complementary portions are base-paired and are covalently linked by a single-stranded "hairpin" area (shRNA).

The siRNA also can be altered RNA that differs from naturally-occurring RNA by the addition, deletion, substitution, and/or alteration of one or more nucleotides. Such alterations can include the addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA also can comprise a 3' overhang. As used herein, a "3' overhang" refers to at least one unpaired nucleotide extending from the 3'-end of a duplexed RNA strand. Thus, in one embodiment, the siRNA comprises at least one 3' overhang of from 1 to about 6 nucleotides (which includes ribonucleotides or deoxyribonucleotides) in length, preferably from 1 to about 5 nucleotides in length, more preferably from 1 to about 4 nucleotides in length, and most preferably from about 2 to about 4 nucleotides in length. In a preferred embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector (e.g., lentiviral, adenoviral, or retroviral vector), as described above for the isolated gene product. Exemplary methods for producing and testing dsRNA or siRNA molecules are described in U.S. Patent Application Publication No. 2002/0173478 and U.S. Pat. No. 7,148,342, the entire disclosures of which are incorporated herein by reference. Examples of shRNA include SEQ ID NOs: 25-27.

Expression of a given gene also can be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alter the activity of the target RNA. Antisense nucleic acids suitable for use in the inventive methods are single-stranded nucleic acids (e.g., RNA, DNA, RNA-DNA chimeras, and peptide-nucleic acids (PNA)) that generally comprise a nucleic acid sequence complementary to a contiguous nucleic acid sequence in a gene product. Preferably, the antisense nucleic acid comprises a nucleic acid sequence that is 50-100% complementary, more preferably 75-100% complementary, and most preferably 95-100% complementary, to a contiguous nucleic acid sequence in a gene product.

Antisense nucleic acids can also contain modifications to the nucleic acid backbone or to the sugar and base moieties (or their equivalent) to enhance target specificity, nuclease resistance, delivery, or other properties related to efficacy of the molecule. Such modifications include cholesterol moieties, duplex intercalators such as acridine, or the inclusion of one or more nuclease-resistant groups.

Antisense nucleic acids can be produced chemically or biologically, or can be expressed from a recombinant plasmid or viral vector, as described above for the isolated gene products. Exemplary methods for producing and testing are within the skill in the art, as disclosed in, for example, Stein, *Science*, 261: 1004 (1993), and U.S. Pat. No. 5,849,902, the entire disclosures of which are incorporated herein by reference.

Expression of a given gene also can be inhibited by an enzymatic nucleic acid. As used herein, an "enzymatic nucleic acid" refers to a nucleic acid comprising a substrate binding region that has complementarity to a contiguous nucleic acid sequence of a gene product, and which is able to specifically cleave the gene product. Preferably, the enzymatic nucleic acid substrate binding region is 50-100% complementary, more preferably 75-100% complementary, and most preferably 95-100% complementary, to a contiguous nucleic acid sequence in a biomarker gene product. The enzymatic nucleic acids also can comprise modifications at the base, sugar, and/or phosphate groups. An exemplary enzymatic nucleic acid for use in the inventive methods is a ribozyme.

The enzymatic nucleic acids can be produced chemically or biologically, or can be expressed from a recombinant plasmid or viral vector, as described above for the isolated gene products. Exemplary methods for producing and testing dsRNA or siRNA molecules are described in Werner, *Nucl. Acids Res.*, 23: 2092-96 (1995); Hammann, *Antisense and Nucleic Acid Drug Dev.*, 9: 25-31 (1999); and U.S. Pat. No. 4,987,071, the entire disclosures of which are incorporated herein by reference.

The inventive compositions can be administered to a subject by any means suitable for directly or indirectly delivering these compositions to the subject (e.g., the lungs, stomach, and/or blood vessels of the subject). For example, the compositions can be administered by methods suitable to transfect cells of the subject with these compositions. Preferably, the cells are transfected with a plasmid or viral vector comprising sequences encoding at least one biomarker gene product or biomarker gene expression inhibiting product.

Transfection methods for eukaryotic cells are well known in the art, and include, e.g., direct injection of the nucleic acid into the nucleus or pronucleus of a cell, electroporation, liposome transfer or transfer mediated by lipophilic materials, receptor-mediated nucleic acid delivery, bioballistic or particle acceleration, calcium phosphate precipitation, and transfection mediated by viral vectors.

For example, cells can be transfected with a liposomal transfer composition, e.g., DOTAP (N-[1-(2,3-dioleoyloxy)propyl]-N,N,N-trimethyl-ammonium methylsulfate, Boehringer-Mannheim) or an equivalent, such as LIPOFECTIN™ Reagent (Invitrogen Corporation). The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

The composition also can be administered to a subject by any suitable enteral or parenteral administration route. Suitable enteral administration routes include, e.g., oral or intranasal delivery. Suitable parenteral administration routes include, e.g., intravascular administration (e.g., intravenous bolus injection, intravenous infusion, intra-arterial bolus injection, intra-arterial infusion, and catheter instillation into the vasculature); subcutaneous injection or deposition, including subcutaneous infusion (such as by osmotic pumps); direct application to the tissue of interest (i.e., lung, liver tissue, etc.), for example by a catheter or other placement device (e.g., an implant comprising a porous, non-porous, or gelatinous material); intramuscular injection; and inhalation.

The composition can be administered to the subject either as naked RNA, in combination with a delivery reagent, or as a nucleic acid (e.g., a recombinant plasmid or viral vector) comprising sequences that express the biomarker gene product or expression inhibiting composition. Suitable delivery reagents include, e.g., the Mirus Transit TKO lipophilic reagent, LIPOFECTIN™ Reagent (Invitrogen Corporation), LIPOFECTAMINE™ (Invitrogen Corporation), CELLFECTIN (Invitrogen Corporation), polycations (e.g., polylysine), and liposomes.

Recombinant plasmids and viral vectors comprising sequences that express the biomarker or biomarker gene expression inhibiting compositions, and techniques for delivering such plasmids and vectors to a tissue, are discussed above.

In a preferred embodiment, liposomes are used to deliver a gene expression-inhibiting composition (or nucleic acids comprising sequences encoding them) to a subject. Liposomes can also increase the blood half-life of the gene products or nucleic acids.

Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka, *Ann. Rev. Biophys. Bioeng.*, 9: 467 (1980); and U.S. Pat. Nos. 4,235,871, 4,501,728, 4,837,028, and 5,019,369, the entire disclosures of which are incorporated herein by reference.

The liposomes can comprise a ligand molecule that targets the liposome to lungs (i.e., small airways and/or large airways). Ligands which bind to receptors prevalent in the lungs, such as monoclonal antibodies that bind small airway epithelial cells, are preferred.

The composition of the invention typically includes a pharmaceutically acceptable carrier. The pharmaceutically acceptable carrier can be any suitable pharmaceutically acceptable carrier, such as one or more compatible solid or liquid fillers, diluents, other excipients, or encapsulating substances which are suitable for administration into a human or veterinary patient. The pharmaceutically acceptable carrier can be an organic or inorganic ingredient, natural or synthetic, with which the active ingredient is combined to facilitate the application of the active ingredient. The pharmaceutically acceptable carrier desirably is co-mingled with one or more of the active components, and with each other, in a manner so as not to substantially impair the desired pharmaceutical efficacy of the active components. Pharmaceutically acceptable carriers desirably are capable of administration to a patient without the production of undesirable physiological effects such as nausea, dizziness, rash, or gastric upset. It is, for example, desirable for the pharmaceutically acceptable carrier not to be immunogenic when administered to a human patient for therapeutic purposes.

The pharmaceutical composition optionally can contain suitable buffering agents, including, for example, acetic acid in a salt, citric acid in a salt, boric acid in a salt, and phosphoric acid in a salt. The pharmaceutical composition also optionally can contain suitable preservatives, such as benzalkonium chloride, chlorobutanol, parabens, and thimerosal.

The pharmaceutical composition conveniently can be presented in unit dosage form and can be prepared by any of the methods well known in the art of pharmacy. Such methods include the step of bringing the active agent into association with a carrier that constitutes one or more accessory ingredients. In general, the composition is prepared by uniformly and intimately bringing the active component(s) into association with a liquid carrier, a finely divided solid carrier, or both, and then, if necessary, shaping the product.

A composition suitable for parenteral administration conveniently comprises a sterile aqueous preparation of the inventive composition, which is preferably isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, including synthetic mono- or di-glycerides. In addition, fatty acids such as oleic acid can be used in the preparation of injectables. Carrier formulations suitable for oral, subcutaneous, intravenous, intramuscular, etc. administrations can be found in Remington's Pharmaceutical Sciences, Mack Publishing Co., Easton, Pa., which is incorporated herein by reference thereto.

The composition of the invention can be in the form of a time-released, delayed release, or sustained release delivery system. The inventive composition can be used in conjunction with other therapeutic agents or therapies. Such an approach can avoid repeated administrations of the inventive composition, thereby increasing convenience to the subject and the physician, and may be particularly suitable for certain compositions of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-, di-, and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active component is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The following examples further illustrate the invention but, of course, should not be construed as in any way limiting its scope.

EXAMPLE 1

This example demonstrates the identification of the CPE splice variant isoform that is a biomarker for cancer metastasis.

Cell Lines.

Three lines of human oral squamous cell carcinoma Tu167, Tu159, and MDA1986 (Myers et al., *Clin. Cancer Res.*, 8: 293-298 (2002)) established from freshly resected human tumors were obtained from the laboratory of Dr. Gary L. Clayman, The University of Texas M.D. Anderson Cancer Center. Human HCC cell lines MHCC97L, MHCC97H, and MHCCLM3 (Li et al., *World J. Gastroenterol.*, 7: 630-636 (2001)) were obtained from Liver Cancer Institute, Fudan University (Shanghai, China). H2P and H2M (Hu et al., *Oncogene*, 23: 298-302 (2004)) were obtained from Dr. X. Y. Guan from the Department of Clinical Oncology, University of Hong Kong. Human prostate adenocarcinoma cell lines (PC3, LNCaP, and DU145), human colon cancer cell lines (HT116, HT29, and SW480), human breast cancer cell lines (MDA-MB-231, T47D, and MCF-7), and Neuro2A cells were obtained from ATCC (Manassas, Va., USA).

Patient Samples.

HCC samples used for Western blotting were obtained with informed consent from 80 patients undergoing hepatectomy for HCC from 2002 to 2005 in the Department of Surgery at the University of Hong Kong (Hong Kong, China). Forty-six of the patients developed recurrence or extrahepatic metastasis within 6 months of surgery, while the other 34 remained disease-free during that time. HCC samples used for RT-PCR and inmmunohistochemistry were obtained with informed consent from 99 patients who underwent surgical resection for HCC from 2000 to 2005 in the Department of Surgery in the University of Hong Kong. Colon cancer samples used for RT-PCR were obtained from 68 patients who underwent surgical resection in 2006 in the Department of Surgery at the University of Hong Kong. Tissue specimens for tissue microarray (TMA) were obtained from 31 patients who underwent surgical operation for colon cancer between 1999 and 2005 at the University of Hong Kong and subsequently developed extra-colonic metastases to liver. Matched pairs of primary and metastatic colon cancer samples were obtained for the TMA.

For prediction of metastasis, CPE-ΔN mRNA from resected primary tumor (T) and surrounding normal tissue (N) from a subset of 37 HCC patients, which showed recurrence or were disease-free, were determined by quantitative RT-PCR (qRT-PCR). A threshold T/N value of 2 was established, above which indicated tumor recurrence within a year. Thereafter 62 and 80 different HCC patients were used in a blinded study as the test groups to measure CPE-ΔN mRNA by qRT-PCR and protein by Western blot, respectively, to predict those patients who would remain disease-free and those patients who would show a recurrence within 2 years (for qRT-PCR) or 6 months (for Western blots) after surgery based on their T/N ratio. A blinded clinical study also was conducted in 68 patients with colon cancer to determine which patients would remain disease-free or would exhibit metastasis/recurrence based on their CPE-ΔN mRNA T/N ratios in the resected tumor and surrounding tissues.

Growth and Proliferation of Neuro2A Clones.

Neuro2A cells were stably transfected with the expression vector, pcDNA3.1/CPE, and selected with 800 μg/ml G418. Individual colonies were picked and screened for the overexpression of CPE from which three clones (clones 3, 6, and 17) were selected (N2A/CPE cells). Neuro2A cells transfected with the pcDNA3.1 empty vector were batch selected with 800 μg/ml G418 and used as control wild-type (WT) Neuro2A cells (WT cells). Cells were plated in 10 cm plates at a density of 6×10$^5$ cells/dish in replicates of 3. Each 10 cm dish contained 6 coverslips. Proliferation was assessed over a period of 4 days with a MTT assay, as described in McGirr et al., *Endocrinology*, 146: 4514 (2005). Briefly, one coverslip was removed from each dish every day and placed into a E-well plate containing 500 μl media. Twenty μl of 2.5 μg/ml thiazolyl blue was added to each well, and cells were incubated for 4 hours at 37° C. Media were removed, and metabolized MTT was dissolved in 200 μl of acidified isopropanol. Absorbance for duplicate 90 μl samples was read at 590 nm in a plate reader.

Bioinformatics.

A non-redundant nucleotide sequence database search was carried out with human and mouse CPE nucleotide sequence as queries (NM_001873.2 and NM_013494.3, respectively). Potential spliced variants (Genbank accession number AK090962 and BY270449) were screened based on difference in nucleotide sequence between the query and the subject sequences. Specific primers at the splice junctions were designed to amplify these variants by PCR in Neuro2A cells and MHCC97 cells for mouse and human splice variants, respectively.

Semi-Quantitative PCR of WT-CPE and CPE-ΔN Transcripts in Neuro2A Clones and HCC Cells.

RNA was extracted from Neuro2A clones, MHCC97L and MHCC97H, using the RNEASY™ Mini Kit (Qiagen, Calif., USA). First strand cDNA was synthesized with 1 μg of total RNA from MHCC97L and MHCC97H cells using Transcriptor First strand cDNA synthesis kit (Roche Applied Science, Germany). Semi-quantitative polymerase chain reaction was performed to quantify CPE-ΔN transcripts using TAKARA™ Taq polymerase (TaKaRa Bio Inc., Shiga, Japan). 18S RNA was used as a housekeeping gene for normalization. Primer sequences specific for human ΔN-splice variant CPE-ΔN RNA were fwd: 5'-ATGGCCGGGCATGAGGCGGC-3' (SEQ ID NO: 5) and rev: 5'-GCTGCGCCCCACCGTGTAAA-3' (SEQ ID NO: 6). Primer sequences specific for mouse ΔN-splice variant CPE-ΔN RNA in Neuro2A cells were fwd: 5'-GACAAAAGAGGCCAGCAAGA-3' (SEQ ID NO: 17) and rev: 5'-CAGGTTCACCCGGCTCAT-3' (SEQ ID NO: 18) and for mouse WT CPE RNA were fwd: 5-TGCTGCTGGCGCTGTGT-3' (SEQ ID NO: 21) and rev: 5'-CAGGTTCACCCGGCTCAT-3' (SEQ ID NO: 22). The primers for mouse WT CPE are specific for WT and do not prime the CPE-ΔN transcript. Primer sequences for amplifying 18S RNA were fwd: 5'-CTCTTAGCTGAGTGTCCCGC-3' (SEQ ID NO: 23) and rev: 5'-CTGATCGTCTTCGAACCTCC-3' (SEQ ID NO: 24). 0.25 μg of cDNA from MHCC97L and MHCC97H cells were used for every reaction. PCR cycling was at 94° C. for 15 seconds, annealing at 65° C. for 30 seconds, extension at 72° C. for 30 seconds and a final extension at 72° C. for 10 minutes. Same conditions were optimized and used for all 3 sets of primers. 16 μl of each sample were removed every 5 cycles from 24 to 35 cycles in each reaction to amplify CPE-ΔN and 18S fragments. Amplified PCR products were separated on 1.5% agarose gels with Tris-borate EDTA buffer and stained with ethidium bromide. Gels were captured as digital images and the corresponding bands quantified by densitometry (ImageJ, NIH).

Verification of the Specificity of CPE-ΔN Specific Primers.

To verify the specificity of the CPE-ΔN primers, the ability of the CPE-ΔN primers to prime and amplify WT CPE transcript obtained from a tissue enriched in CPE was assayed. Normal human adrenal medulla where CPE is expressed in abundance was utilized. First strand cDNA was synthesized from 100 ng of total RNA from this tissue using the Transcriptor First strand cDNA synthesis kit (Roche Applied Science, Germany). The semi-quantitative polymerase chain reaction was performed with TAKARA™ Taq polymerase (TaKaRa Bio Inc., Shiga, Japan) with 35 PCR cycles at 94° C. for 15 seconds, annealing at 65° C. for 30 seconds, extension at 72° C. for 30 seconds, and a final extension at 72° C. for 10 minutes. The PCR was carried out with both generic CPE primers (fwd: 5'-CCATCTCCGTGGAAGGAATA-3' (SEQ ID NO: 11) and rev: 5'-CCTGGAGCTGAGGCTGTAAG-3' (SEQ ID NO: 12)) and CPE-ΔN specific primers (fwd: 5'-ATGGCCGGGCATGAGGCGGC-3' (SEQ ID NO: 5), rev: 5'-GCTGCGCCCCACCGTGTAAA-3' (SEQ ID NO: 6)). The correctly sized product was amplified using the generic primers, but no product was amplified with the CPE-ΔN specific primers, which indicated that the CPE-ΔN primers are specific for CPE-ΔN cDNA.

Verification of Lack of CPE WT in HCC Cells and Human HCC Tumors.

Since primers that specifically amplified the human WT CPE mRNA were not identified, an alternative method was used to determine if MHCC97H cells contain WT CPE. A standard curve was generated, so that the amount of template in an unknown sample in terms of copy number could be determined. A complete clone of hCPE cDNA was excised from its plasmid and purified, and its concentration was determined spectophotometrically. Serial dilutions of the cDNA were made and used as templates for qRT-PCR. The PCR was carried out in triplicate for each sample from eight different concentrations. Generic CPE primers were used, and the crossing point was determined from the qRT-PCR program, averaged for each point, plotted as a function of the starting template concentration, and expressed as template copy number. The mRNA copy numbers in the MHCC97H cells or HCC tumor tissue were compared using the set of generic primers (fwd: 5'-CCATCTCCGTGGAAGGAATA-3' (SEQ ID NO: 11) and rev: 5'-CCTGGAGCTGAGGCTGTAAG-3' (SEQ ID NO: 12)) that amplifies both WT and CPE-ΔN cDNA and using primers specific for hCPE-ΔN (fwd: 5'-ATGGCCGGGCATGAGGCGGC-3' (SEQ ID NO: 5) and rev: 5'-GCTGCGCCCCACCGTGTAAA-3'(SEQ ID NO: 6)). Conditions for the qRT-PCR for CPE using both sets of primers were as follows: initial denaturation for 3 minutes at 95° C., followed by 45 cycles of 15 seconds at 95° C., 15 seconds at 62° C., a seconds at 72° C. The PCR reaction was followed by a melting curve program (65° C.-95° C.) with a heating rate of 0.1° C. per second, a continuous fluorescence measurement, and a cooling program at 40° C. Negative controls consisting of no-template (water) reaction mixtures were run with all reactions. PCR products also were run on agarose gels to confirm the formation of a single product of the predicted size. The copy numbers in the HCC cells and the human tumor samples using either the generic primers or the CPE-ΔN specific primers were identical, indicating that MHCC97H cells and HCC tumors lacked WT CPE. Additionally, Western blots of MHCC97H cells and human HCC samples using AtT-20 cells as a positive control showed no WT CPE band.

Microarray Hybridization and Data Analysis of Neuro2A Cells.

Neuro2A clonal cells expressing CPE and the WT cells transfected with vector alone were used for microarray studies. All GeneChips were processed at the London Regional Genomics Centre (Robarts Research Institute, London, Ontario, Canada). RNA was extracted from clone 17, and the WT cells and the quality of the RNA was assessed using the Agilent 2100 Bioanalyzer (Agilent Technologies Inc., Palo Alto, Calif., USA) and the RNA 6000 Nano kit (Caliper Life Sciences, Mountain View, Calif., USA). All procedures, including cRNA synthesis, labeling, and hybridization to Affymetrix Mouse Genome 2.0 GeneChips, were performed as described in the Affymetrix Technical Analysis Manual (Affymetrix, Santa Clara, Calif., USA). GeneChips were scanned with the Affymetrix GeneChip Scanner 3000 (Affymetrix, Santa Clara, Calif., USA). Probe signal intensities for genes were generated using GCOS1.4 (Affymetrix Inc., Santa Clara, Calif., USA) using default values for the statistical expression algorithm parameters and a target signal of 150 for all probe sets and a normalization value of 1. Gene level data was generated using the RMA preprocessor in GeneSpring GX 7.3.1 (Agilent Technologies Inc., Palo Alto, Calif., USA). Data from 4 different microarrays were transformed (measurements less than 0.01 set to 0.01) and normalized per chip to the 50th percentile and per gene to the WT Neuro2A cells. Genes were grouped according to function in development and considered significantly changed using Venn analysis to screen at least 2-fold changes, followed by a one-way ΔNOVA with a p value cutoff of 0.05.

Western Blot for CPE-ΔN and NEDD9 in Cell Lines and Clinical Specimens.

Proteins from clinical specimens were prepared using urea buffer (8 M urea, 10 mM Tris, pH 7). Briefly, frozen tissue blocks were homogenized, and cells were placed on ice for 15 minutes and then centrifuged at 13,000×g for 5 minutes at 4° C. The protein supernatant was collected, and its concentration was determined. Proteins from human cancer cell lines were prepared using cell lysis buffer (Cell Signaling Technology, Beverly, Mass., USA) or, for Neuro2A cells, with M-per mammalian protein extraction reagent (Pierce, Rockford, Ill., USA) supplemented with Complete Inhibitor Cocktail (Roche, Indianapolis, Ind., USA) to prevent protein degradation. The cell lysate was collected and centrifuged at 15,000×g for 10 minutes at 4° C. The protein concentrations from supernatants of the cell lysates were determined. Twenty μg of protein were denatured, run on 4-20% or 12% SDS-PAGE gels, and transferred onto nitrocellulose membrane or PVDF membrane (Millipore, Billerica, Mass., USA) using the standard protocol. After blocking with 5% nonfat milk at room temperature for 1 hour, CPE-ΔN on the membrane was detected using a CPE monoclonal antibody directed against amino acid residues 49-200 of the human WT CPE sequence (R&D Systems, Inc., Minneapolis, Minn.) at 1:4000 dilution. NEDD9 was detected with mouse anti-human HEF1 generated using the N-terminal 82-398 residues of the NEDD9 protein (clone 14A11 at 1:1000 dilution, Rockland Immunochemicals, Gilbertsville, Pa., USA) and rabbit polyclonal C-terminal antibody from Professor Mirimoto (Japan) (Sasaki et al., *Stroke*, 36: 2457 (2005)). Following primary antibody binding, the membrane was incubated with horseradish peroxidase-conjugated anti-mouse or rabbit antibody (Amersham) and then visualized by enhanced chemiluminescence plus according to the manufacturer's protocol. The intensity of the bands was quantified by densitometry and expressed as arbitrary unites (AU). The expression of CPE-ΔN and NEDD9 levels of each cell line was corrected for their actin level and expressed as the mean±SEM of AU from three separate experiments.

Lentiviral Based CPE-ΔN Suppression in Tumor Cell Lines.

Lentiviral based shRNAs against human CPE, which also suppress CPE-ΔN mRNA expression (CCGGCCAGTAC-CTATGCAACGAATACTCGAGTATTCGT-TGCATAGGTACTGGTTTTT G (SEQ ID NO: 25); CCG-GCTCCAGGCTATCTGGCAATAACTCGAGTTATTGC-CAGATAGCCTGGAGTTTTT G (SEQ ID NO: 26); and CCGGGATAGGATAGTGTACGTGAATCTC-GAGATTCACGTACACTATCCTATCTTTTT G (SEQ ID NO: 27)) and scramble control were obtained from DFCI-Broad RNAi Consortium in a pLKO.puro vector. VSV.G-pseudotyped lentiviral particles were generated by calcium phosphate cotransfection of 293T cells, and viral supernatants were collected after 48 hours. Lentiviral supernatants were used to transduce (i) MHCCLM3, (ii) HT29, (iii) MDA-MB-231, (iv) DU145, and (v) MDA1986 cells. At 2 days post-transduction, cells were selected by puromycin at a concentration of 2 μg/ml.

Immunofluorescence of CPE-ΔN in HCC Tumor Cells.

MHCCLM3 cells transfected with either si-scrambled or si-CPE-ΔN (which down-regulates CPE-ΔN mRNA expression) were cultured on chamber slides, permeabilized with 0.1% Triton X-100, and fixed with 4% paraformaldehyde in PBS. The cells were incubated with monoclonal antibodies against CPE (1:100) (R&D Systems, Inc., Minneapolis, Minn., USA). The secondary antibody was TRITC—conjugated goat anti-mouse IgG (Molecular Probes). The slide was subsequently stained with fluorescein phalloidin (Molecular Probes) in 1% BSA (dilution factor, 1:50) at 37° C. for 1 hour and counterstained by DAPI (AppliChem GmbH). All images were visualized by confocal microscopy and photographs were taken at 600× magnification.

Colony Formation Assay.

Growth analysis of cells was performed by the colony formation assay described Ng et al., *Cancer Res.*, 60: 6581-6584 (2000). Eighty percent confluent cells were trypsinized, and single-cell suspensions were obtained. Four hundred viable cells were seeded per well in 6-well plates. Ten days later, cells were fixed with 70% ethanol and stained with 10% (v/v) Giemsa (MERCK, Damstadt, Germany). Colonies consisting of more than 50 cells were counted. Each experiment was done in triplicate, and the mean values±SEM were determined.

Matrigel Invasion Assay.

Invasion assay was carried out as described in Lee et al., *Cancer Res.*, 66: 9948-9956 (2006). Conditioned medium from cells transfected with si-scramble or si-CPE-ΔN was placed in the lower chambers as chemo-attractants. After 22 hours in culture, the cells were removed from the upper surface of the filter by scraping with a cotton swab. The cells that invaded through the Matrigel and were adherent to the bottom of the membrane were stained with crystal violet solution. The cell-associated dye was eluted with 10% acetic acid, and its absorbance at 595 nm determined. Each experiment was done in triplicate, and the mean values±SEM were determined.

Generation of Luciferase-Expressing Cells.

For luciferase labeling of MHCCLM3 cells, lentiviral vector containing the sequence of the firefly luciferase gene was constructed and transfected into the cells (see, e.g., Lee et al., *Cancer Res.*, 67: 8800 (2007)). Stable transfectants were generated from a pool of >20 positive clones, which were selected by blasticidin at a concentration of 2 μg/ml.

Bioluminescent Imaging of Live Animals Bearing Tumors.

Animal care and euthanasia were conducted with full approval by the Committee on the Use of Live Animals in Teaching and Research of the University of Hong Kong. Approximately 1×10$^6$ MHCCLM3 cells stably expressing firefly luciferase were transfected with either si-scramble or si-CPE-ΔN and injected subcutaneously into the right flank of four-week-old male BALB/c-nu/nu mice with a 30-gauge hypodermic needle (see, e.g., Fu et al., *Proc. Natl. Acad. Sci. U.S.A.*, 88: 9345 (1991)). The mice were imaged on day 0 and day 30 after cell inoculation. Mice were anesthetized with ketamine-xylazine mix (4:1). Imaging was done using an Xenogen IVIS™ 100 cooled CCD camera (Caliper Life Sciences, Hopkinton, Mass., USA). The mice were injected with 200 μL of 15 mg/ml D-luciferin i.p. for 15 minutes before imaging, after which they were placed in a light-tight chamber. A gray-scale reference image was obtained followed by the acquisition of a bioluminescent image. The acquisition time ranged from 3 seconds to 1 minute.

Metastatic Orthotopic Nude Mouse Model.

Approximately 1×10$^6$ MHCCLM3 cells (in 0.2 ml culture medium) transfected with either si-scramble or si-CPE-ΔN were injected subcutaneously into the right flank of nude mice, which were then observed daily for signs of tumor development. Once the subcutaneous tumor reached 1 to 1.5 cm in diameter, the tumor was removed and cut into about 1 to 2 mm cubes, which were implanted into the left liver lobe of the nude mice (see, e.g., Livak et al., *Methods*, 25: 402 (2001)). The mice were imaged on day 0 and day 35 after tumor inoculation. Mice were anesthetized with ketamine-xylazine mix (4:1). Imaging was performed using a Xenogen IVIS 100 cooled CCD camera (Xenogen) and metastasis to the lung and intestines was tracked. After imaging, metastasis to these tissues was confirmed by inspection and imaging of the dissected tissues.

Histopathology.

To confirm that metastasis to the lungs occurred, the animal was autopsied as soon as the original signal was recorded. Lungs were examined and imaged with the Xenogen camera to confirm the bioluminescence of this tissue and then fixed by intrabranchial perfusion of 10% neutralized formalin solution. Paraffin-embedded sections (4 μm) were cut and stained with H&E.

Quantitative RT-PCR of CPE-ΔN in Cell Lines and Clinical Specimens.

RNA was extracted from both cancer cells (as described above) and each patient's tumor and surrounding non-tumor tissue using trizol (Invitrogen, Calif., USA). Complementary DNA amplified from 0.2 μg mRNA in the tissues was subjected to real-time quantitative PCR for CPE-ΔN expression using a Fast SYBR™ Green Master Mix PCR kit (Applied Biosystems, Foster City, Calif., USA) under the following cycling conditions: 95° C. for 5 mins, followed by 40 cycles of 95° C. for 15 second, 62° C. for 60 seconds. Reactions were performed using an ABI PRISM 7900 Sequence Detector (Applied Biosystems). Fluorescence signals were analyzed using SDS 1.9.1 software (Applied Biosystems). 18S was used as the endogenous normalization control. Primer sequences for CPE-ΔN RNA were fwd: 5'-ATGGC-CGGGCATGAGGCGGC-3' (SEQ ID NO: 5), rev: 5'-GCT-GCGCCCCACCGTGTAAA-3' (SEQ ID NO: 6); 18S-fwd: 5'-CTCTTAGCTGAGTGTCCCGC-3' (SEQ ID NO: 23); and 18S-rev: 5'-CTGATCGTCTTCGAACCTCC-3' (SEQ ID NO: 24). All PCRs were performed in duplicate and were averaged to obtain the data point for each specimen. The relative amount of CPE-ΔN mRNA was normalized to an internal control, 18S, and relative to a calibrator (see, e.g., Livak et al., *Methods*, 25: 402 (2001)): $2^{-\Delta\Delta C_T}$, where $\Delta\Delta C_T = [C_T(CPE) - C_T(18S)]\text{test} - [C_T(CPE) - C_T(18S)]\text{calibrator}$. The threshold value ($C_T$) was defined as the fractional cycle number at which the amount of amplified target reached a fixed threshold. The $C_T$ value correlated with the input target mRNA levels, and a lower $C_T$ value indicated a higher starting copy number. One of the samples was designated as the calibrator to compare the relative amount of target in different samples and used to adjust for the plate-to-plate variation in amplification efficiency. The relative expression level of CPE of each patient was evaluated as the relative fold change in log 2 scale.

Construction of Tissue Microarray (TMA).

Tissue microarrays were constructed with 0.6 mm diameter cores using a MTA-1 tissue arrayer (Beecher Instruments, Sun Prairie, Wis.) (see, e.g., Kononen, *Nat. Med.*, 4: 844-847 (1998)). The final array contained 31 pairs of primary and matched metastatic colorectal to liver cancer samples. Five μm sections were cut and immunostained as described below. Regions of interest were selected from hematoxylin and eosin stained sections after review by two pathologists.

Immunostaining and Quantification of CPE in Human Tissue Sections.

HCC tumor tissue and surrounding non-tumor tissue were formalin-fixed and paraffin-embedded. Four μm sections were cut, dewaxed in xylene and graded alcohols, hydrated, and washed in PBS. After pretreatment in a microwave oven (12 minutes in sodium citrate buffer (pH 6)), the endogenous peroxidase was inhibited by 0.3% $H_2O_2$ for 30 min, and the sections were incubated with 10% normal goat serum for 30 minutes. Mouse monoclonal anti-carboxypeptiase E (1:100) (R&D Systems, Inc., Minneapolis, Minn.) was applied overnight in a humidity chamber at 4° C. A standard avidin-biotin peroxidase technique (DAKO, Carpinteria, Calif.) was applied. Briefly, biotinylated goat anti-mouse immunoglobulin and avidin-biotin peroxidase complex were applied for 30 minutes each with 15-minute washes in PBS. The reaction was finally developed with the Dako Liquid DAB+ Substrate Chromogen System (Dako, Glostrup, Denmark). Slides were imaged on a SCANSCOPE™ CS imager (Aperio, Vista, Calif., USA), generating 0.43 μm/pixel whole slide images. These images were compiled and analyzed using the SPECTRUM™ software (Aperio, Vista, Calif., USA) with a pixel count algorithm (see, e.g., Brennan et al., *Clin. Cancer Res.*, 14: 2681 (2008)). Quantified expression of tumor tissue minus adjacent normal tissue was compared for patients with and without recurrence.

Results.

In order to investigate the possible role of CPE, wild-type (WT) CPE cDNA was stably transfected into a clone of the mouse neuroblastoma cell line, Neuro2A, with low CPE expression. The isolated clones proliferated faster than Neuro2A cells transfected with empty vector (see FIG. 5A).

This result prompted an exhaustive non-redundant nucleotide sequence database search that uncovered a splice variant isoform of CPE that lacks the N-terminus (CPE-ΔN) (see FIG. 5B). PCR identified two different CPE transcripts expressed in the stably transfected Neuro2A clones: WT and CPE-ΔN (see FIG. 5B). This finding suggested that CPE-ΔN is responsible for the enhanced proliferation of Neuro2A cells.

To identify genes up-regulated in the CPE-transfected Neuro2A clones that promote proliferation, gene microarray analysis of a Neuro2A clone stably overexpressing CPE versus WT Neuro2A cells transfected with empty vector was performed. The analysis showed, among changes in other mRNAs, a 6-fold higher expression of NEDD9 in the CPE-transfected Neuro2A clone. NEDD9 has been shown to be expressed during embryonic development, and expression of NEDD9 is down-regulated in adult mice (see, e.g., Kumar et al., *Biochem. Biophys. Res. Commun.*, 185: 1155 (1992); and Aquino et al., *Gene Expression Patterns*, 8: 217 (2008)). NEDD9 has been implicated in cancer development (see, e.g., Merrill et al., *Dev. Dyn.*, 231: 564 (2004); and O'Neill et al., *Cancer. Res.*, 67: 8975 (2007)) and recently was identified as a metastasis promoting gene in melanomas (see, e.g., Kim et al., *Cell*, 125: 1269-81 (2006)). NEDD9 promoted growth and enhanced invasion in vitro and metastasis in vivo of normal and transformed melanocytes by interacting with focal adhesion kinase (FAK) (see, e.g., Kim, *Cell*, 125: 1269-81 (2006); and McLean et al., *Nat. Rev. Cancer*, 5: 505 (2005)). NEDD9 is highly expressed in human melanomas and governs the metastatic potential of these tumors.

These findings led to the hypothesis that CPE-ΔN promotes growth and metastasis of tumor cells by up-regulating NEDD9 gene expression. This hypothesis was tested on human HCC cells. Semi-quantitative RT-PCR showed that high metastatic MHCC97H cells had elevated levels of CPE-ΔN mRNA compared to low metastatic cells (MHCC97L) (see FIG. 6). Moreover, WT CPE mRNA or protein was not expressed in these epithelial-derived MHCC97 cells, unlike neuroendocrine tumors, which express both WT and CPE- ΔN. Quantitative RT-PCR showed that CPE-ΔN mRNA was 8.5-fold higher in MHCC97H versus MHCC97L cells (see FIGS. 7A-E).

The translation product derived from the human CPE-ΔN splice variant transcript (see FIG. 6) in HCC cells has an apparent molecular mass of ~40 kD. Other highly metastatic human tumor cell lines of epithelial origin derived from HCC, colon, breast, prostate, and head and neck tumors also had elevated expression of CPE-ΔN mRNA (see FIGS. 7A-E) and the ~40 kD CPE-ΔN protein, as well as NEDD9 protein, compared to matched tumor lines with low metastatic potential (see FIGS. 1A-E). The forms of NEDD9 that increased with metastatic potential in these cells were primarily a 70 kD N-terminal domain that contains the FAK binding domain involved in metastasis (see, e.g., O'Neill et al., *Mol. Cell Biol.*, 15: 5094 (2001)) and a 35 kD C-terminal cleavage product.

Figure 1B:
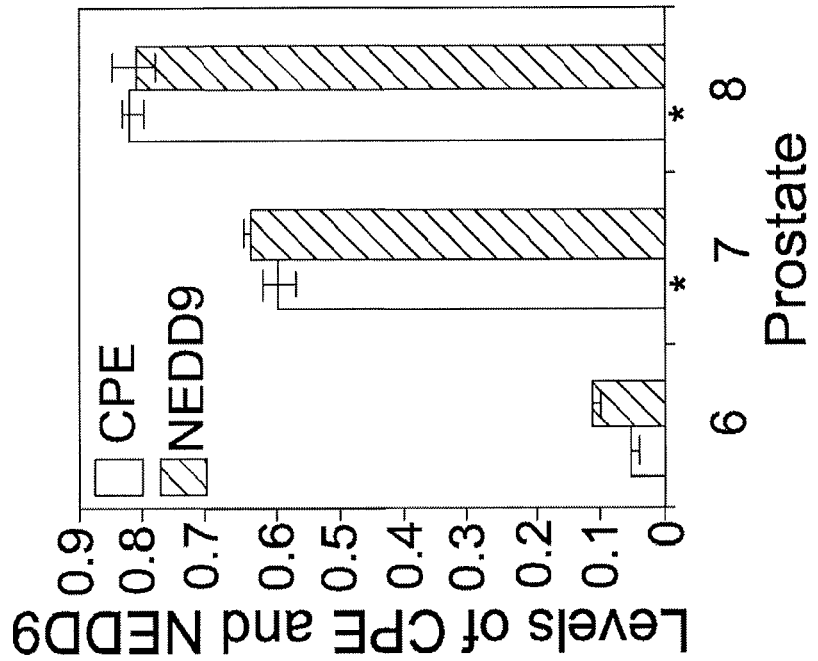
Figure 1A:
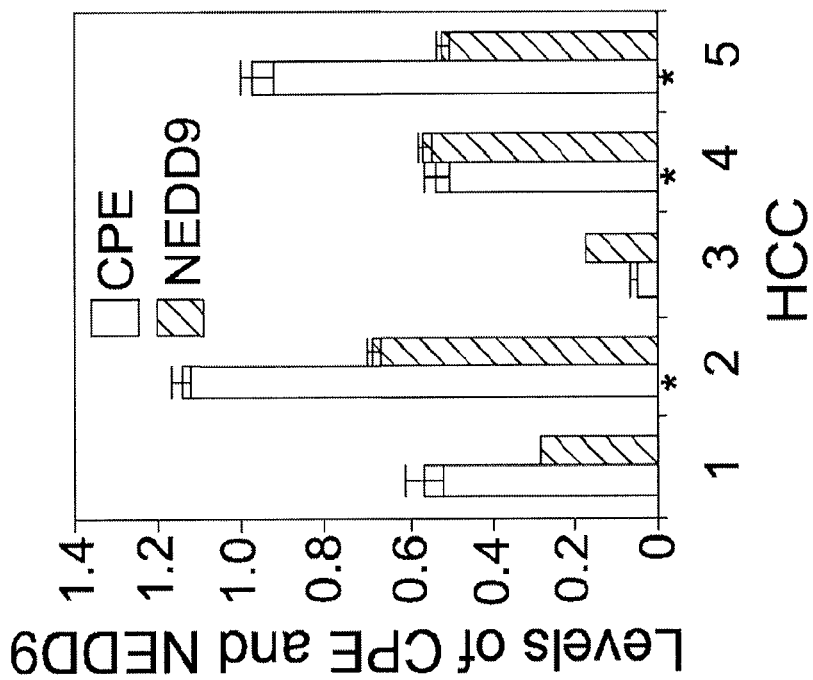
Figure 1D:
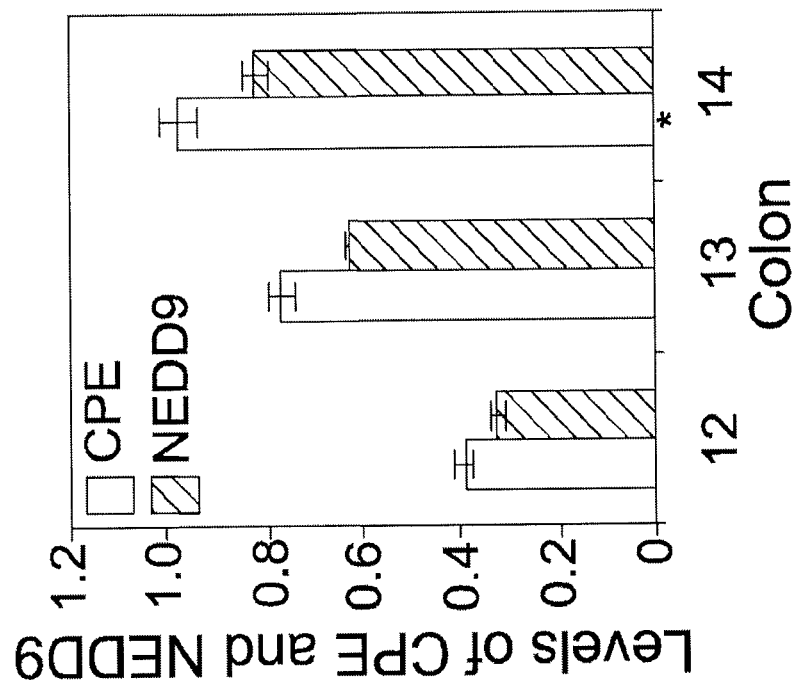
Figure 1C:
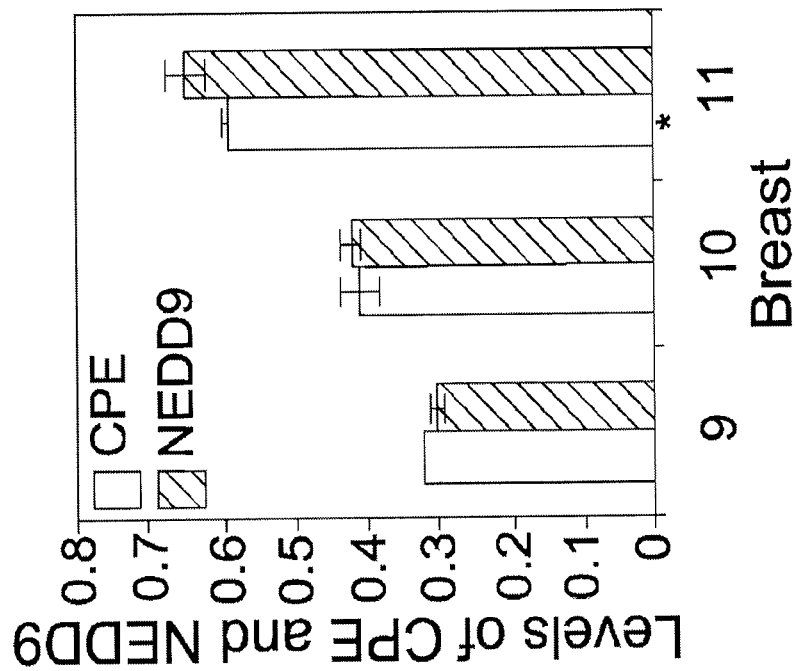
Figure 1E:
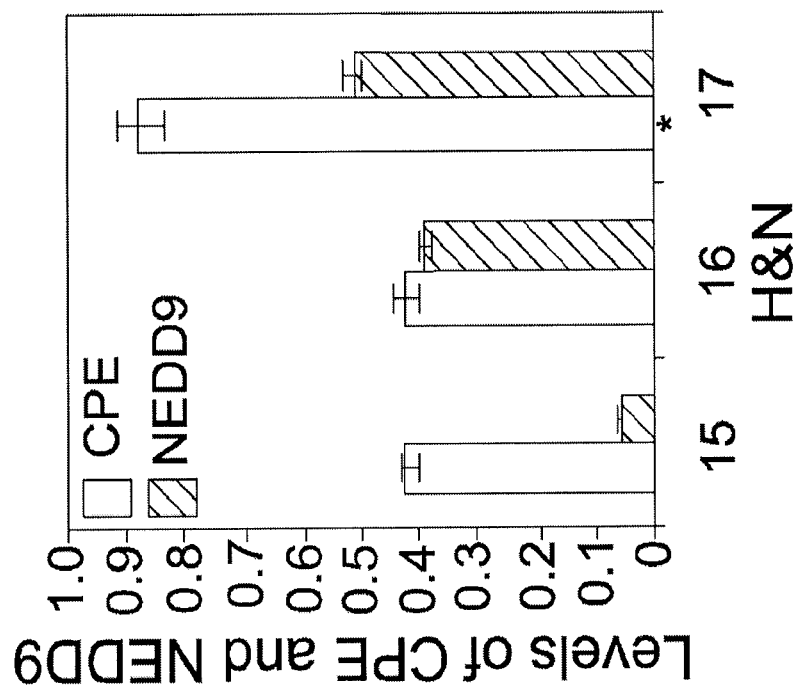
Figure 2A:
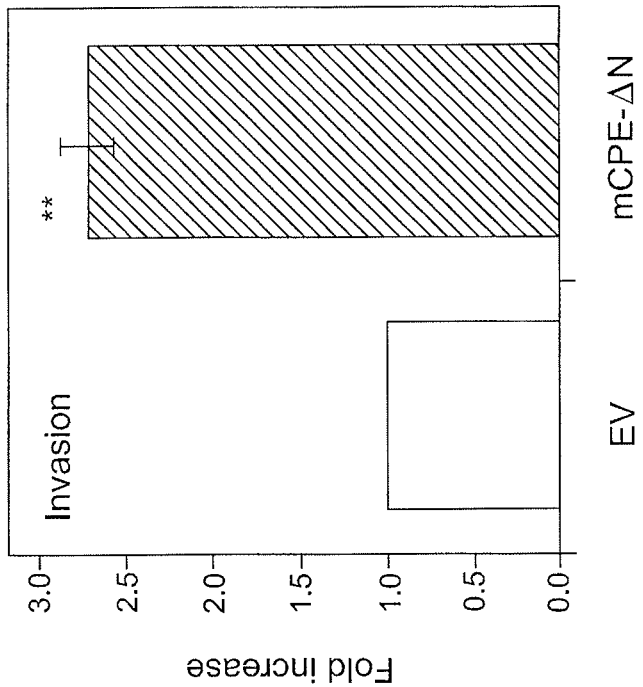
Figure 2B:
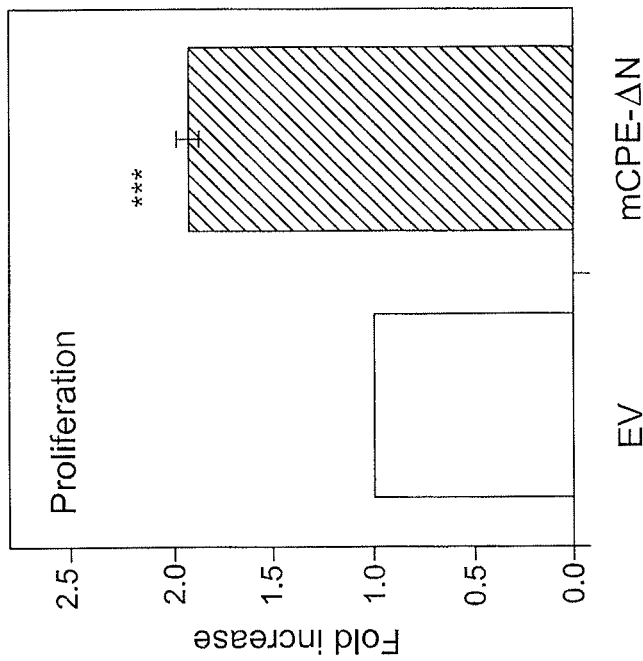

To verify that CPE-ΔN regulates NEDD9 gene expression, low metastatic MHCC97L cells were transfected with the CPE-ΔN cDNA. A concomitant increase in CPE-ΔN and NEDD9 protein was observed. Furthermore, MHCC97L cells transfected with CPE-ΔN showed increased proliferation and invasion compared to cells transfected with empty vector, thereby demonstrating a role of CPE-ΔN in growth promotion and invasion of tumor cells (see FIGS. 2A-B).

Conversely, siRNA-mediated down-regulation of CPE-ΔN in the highly metastatic MHCCLM3 cells resulted in a decrease in NEDD9 expression in each of the 3 clones stably transfected with 3 different si-RNA sequences. Immunofluorescence microscopy of MHCCLM3 cells transduced with scrambled-si (si-scr) RNA revealed immunoreactive CPE-ΔN primarily in the nucleus versus cytoplasm. In MHCCLM3 cells down-regulated in expression of CPE-ΔN by si-CPE-ΔN, CPE-ΔN immunofluorescence was barely detectable. These results indicate that CPE-ΔN that lacks a signal peptide is expressed in the cytoplasm and can be translocated into the nucleus to modulate gene expression.

To demonstrate that CPE-ΔN mediates growth and cell invasion in multiple types of human tumors, highly metastatic cell lines from breast (MDA-MB-23), prostate (DU145), head and neck (MDA 1986), colon (HT29), and liver (MHCC97M3) were down-regulated in CPE-ΔN expression using si-RNA (SEQ ID NO: 26) (see FIG. 3A). Suppression of CPE-ΔN expression in these tumor cell lines led to 56-85% inhibition of growth (FIG. 3B) and 70-85% inhibition of invasion (see FIG. 3B).

In addition to the in vitro assays, in vivo animal studies were performed in two models. Nude mice were subcutaneously injected with MHCCLM3 cells transduced with either si-CPE-ΔN (SEQ ID NO: 26) or si-scr (see, e.g., Lee et al., *Clin. Cancer Res.*, 11: 8458 (2005)). Thirty days after cell inoculation, control mice injected with the si-scr MHCCLM3 cells had liver tumors with 16.2-fold higher intensity (which reflects increased volume) when compared to mice injected with si-CPE-ΔN cells.

Using a metastatic orthotopic nude mouse model (see, e.g., Lee et al., *Cancer Res.*, 67: 8800 (2007)), MHCCLM3 cells transduced with either si-scr or si-CPE-ΔN were injected subcutaneously into the right flank of the mice. When the subcutaneous tumor was ~1.5 cm in diameter, the tumor was removed, cut into 1-2 mm cubes, and implanted into the liver of nude mice (see, e.g., Lee et al., *Cancer Res.*, 67: 8800 (2007)). Thirty-five days post-implantation, mice with the si-scr MHCCLM3-derived tumors showed 13.9-fold higher intensity (reflecting increased volume) and developed intrahepatic metastasis and extrahepatic metastasis to lung and intestine (see, e.g., Li et al., *Clin. Cancer Res.*, 12: 7140 (2006)), while mice inoculated with si-CPE-ΔN MHC-CLM3-derived tumors had smaller tumors and failed to demonstrate metastasis.

To determine if CPE-ΔN is a useful marker for predicting future recurrence and metastasis, quantitative RT-PCR and Western blot analysis were performed on primary tumors from HCC patients to measure CPE-ΔN mRNA and protein levels, respectively. RT-PCR verified that only CPE-ΔN mRNA, and not WT CPE mRNA, was expressed in primary HCC tumors. CPE-ΔN was quantified by qRT-PCR in the primary tumor (T) versus surrounding non-tumor (N) tissue, and its ratio determined. Forty-four of 49 (89.8%) HCC patients, who were disease-free two years after surgery, had CPE-ΔN mRNA T/N ratios of ≤2. In contrast, 46 of 50 (92%) of patients with extra- or intra-hepatic metastasis/recurrence had a T/N ratio>2 (see FIG. 4A and Table 1).

TABLE 1

Clinical significance of CPE in HCC tissues.

| Clinicopathological Variables | n | CPE Expression T/NT ≤ 2 | T/NT > 2 | p value |
|---|---|---|---|---|
| TNM (UICC) classification | | | | |
| Early Stage (I-II) | 39 | 26 | 13 | <0.002*+ |
| Late Stage (III-IV) | 57 | 20 | 37 | |
| Recurrence in the first year | | | | |
| Yes | 50 | 4 | 46 | <0.001* |
| No | 49 | 44 | 5 | |

*statistically significant;
+incomplete data

The survival analysis of disease-free survival of 99 HCC patients showed shorter survival times (p<0.0001) when CPE-ΔN mRNA T/N were >2 (high) in the primary tumor compared to patients with T/N≤2 (low). The mean survival was 17.44 months and 82.75 months for the high group versus the low group.

In 68 colorectal cancer patients, the level of CPE-ΔN was determined at the time of surgery. Twenty-nine of 31 (93.5%) patients that were disease-free had a CPE-ΔN mRNA T/N ratio of ≤2, whereas 32 of 37 (86.5%) patients that had lymph node or distant metastasis had a CPE-ΔN mRNA T/N ratio of >2 (see Table 2).

TABLE 2

Clinical significance of CPE in colorectal cancer.

| Clinicopathological Variables | n | CPE Expression T/NT ≤ 2 | T/NT > 2 | p value |
|---|---|---|---|---|
| TNM (UICC) classification | | | | |
| Early Stage (I-II) | 29 | 28 | 1 | <0.001* |
| Late Stage (III-IV) | 39 | 6 | 33 | |
| Lymph node and distant metastases | | | | |
| Yes | 37 | 11 | 26 | <0.001* |
| No | 31 | 26 | 5 | |

*statistically significant

Additionally, Western blots showed higher CPE-ΔN levels in patients with recurrence compared to the disease-free group. Quantitative analysis of the T/N ratios of the CPE-ΔN band from Western blots from 80 patients revealed that 28 of 34 (82.3%) patients with primary HCC who were disease-free after surgery had tumor CPE-ΔN levels with T/N≤2 (see FIG. 4B). However, 35 of 46 (76%) patients who developed intrahepatic recurrence or extra-hepatic metastasis within 6 months had primary tumor CPE-ΔN levels of T/N>2.

Immunohistochemistry (IHC) of CPE-ΔN in HCC tumors from patients revealed immunostaining primarily in the nuclei of tumor cells in patients who subsequently developed recurrence that was absent in the cell nuclei of patients who remained disease-free. Staining was primarily in the cytoplasm of tumor cells in patients who remained disease-free. The intensity of immunostaining as determined by image analysis (0.402±0.032 SEM versus 0.279±0.036 SEM) was statistically different (p<0.02) between the groups.

Analysis of primary colorectal cancer cells that had metastasized to the liver also revealed increased numbers of CPE-ΔN positive cells in the metastatic tissue, and, similar to the HCC cells, staining was observed primarily in the nuclei of these metastatic colorectal cells.

These retrospective studies demonstrate that measurement of CPE-ΔN mRNA and protein levels in resected tumors is a powerful prognostic tool for predicting recurrence/metastasis in cancer (e.g., HCC) patients. In particular, measurement of CPE-ΔN mRNA levels in resected primary tumors versus surrounding non-tumor tissues from HCC and PHEO/PGL patients by qRT-PCR has proven to be a very reliable tool for predicting future metastasis/recurrence with high prognostic significance (p<0.0001).

The data resulting from these in vitro and in vivo assays demonstrate that CPE-ΔN functions to govern growth, invasion, and metastasis in multiple types of cancer cells, including liver, breast, colorectal, and head and neck cancers, by up-regulating the metastasis gene NEDD9, which has been shown to promote growth and metastasis of melanoma cells. The results from CPE-ΔN analysis of clinical resected primary and metastatic tumors from colorectal cancer and HCC patients demonstrate that CPE-ΔN can serve as a biomarker for metastasis and a reliable predictor of impending metastasis within 6 months of diagnosis of HCC based on CPE-ΔN levels in the resected primary HCC tumor.

CPE-ΔN is translocated into the nucleus and has a domain homologous to histone deacetylase (HDAC) interacting proteins (human CPE-ΔN amino acids 111 to 196 with a consensus of 60%). The results of co-immunoprecipitation studies indicated that CPE-ΔN interacts with HDAC1/2, which are known to modulate gene transcription through histone deacetylation and mediate human tumorigenesis. When HCC97L cells stably expressing CPE-ΔN were treated with the HDAC inhibitors, depsipeptide and TSA, expression of NEDD9 in the HCC cells was suppressed while there was no effect on CPE-ΔN expression. Based on these results, CPE-ΔN appears to upregulate NEDD9 gene expression through its interaction with HDAC1/2 to induce tumor cell proliferation and migration.

EXAMPLE 2

This example demonstrates that the expression level of CPE-ΔN is correlated with metastasis.

Paragangliomas (PGLs) are catecholamine-producing neuroendocrine tumors that derive from sympathetic tissue in adrenal (also known as pheochromocytomas (PHEOs)) and extra-adrenal locations or from parasympathetic tissue of the head and neck. Despite improved diagnostic techniques there is generally a 3-year delay between the initial symptoms and final diagnosis of PGL. Advances in genetic testing have led to the recognition of the high prevalence of PGLs in certain familial syndromes. The accumulation of evidence now indicates that the hereditary basis of PGLs accounts for 24% of patients with the tumor, with no obvious initial evidence of a syndrome or family history. Germline mutations in five genes have been associated with familial syndromes: the von Hippel-Lindau gene (VHL), which causes von Hippel-Lindau syndrome; the RET gene leading to multiple endocrine neoplasia type 2 (MEN2); the neurofibromatosis type 1 gene (NF1), which is associated with von Recklinghausen's disease; and the genes encoding the B and D subunits of mitochondrial succinate dehydrogenase (SDHB and SDHD), which are associated with familial PGLs and PHEOs. PHEOs are not always present and usually are not the first clinical manifestation of syndromes due to mutations of VHL, RET, and NF1 genes. PHEOs in these three syndromes usually are associated with other benign or malignant neoplasms.

Prevalence of metastasis is much higher for patients with specific mutations such as those causing some form of PGL (e.g., SDHB). SDHB/SDHD patients develop PHEOs, head and neck tumors, and abdominal PGLs. There are three genes involved in the pathogenesis of familial PGL syndrome described to date: those encoding the B, C and D subunits of mitochondrial complex II enzyme succinate dehydrogenase (SDHB, SDHC, and SDHD). SDHD/C-associated tumors are predominantly benign; however, SDHB mutations predispose to malignant PGL with poor prognosis. Up to 70% of abdominal and thoracic PGLs in patients carrying a SDHB mutation were reported to develop into metastatic disease. Currently, there is no marker available that would either predict malignant behavior or diagnose malignancy of these tumors. Furthermore, the diagnosis of SDHB-related PGL may be delayed by lack of typical symptoms and signs of catecholamine excess.

To determine the copy numbers of CPE-ΔN mRNA in resected tumors from patients, mRNA was extracted from frozen resected tumor tissues from patients using the SV Total RNA Isolation System (Promega, USA) according to manufacture's instructions. 0.2 μg of total mRNA was converted to cDNA using the First Strand cDNA Synthesis Kit for RT-PCR (Roche Applied Sciences, Germany). 0.25 μg of the first strand cDNA was used to determine the CPE-ΔN mRNA copy number in the samples by absolute quantification obtained from a standard curve generated for every assay. The standard curve was generated using defined concentrations of full-length CPE-WT cDNA cloned in pcDNA3.1 His vector (Invitrogen, USA). The CPE-WT cDNA sequence was cleaved from pcDNA3.1 CPE-WT cDNA by XhoI and BamHI restriction enzymes, and the digest run on a 1.5% agarose gel. The CPE-WT cDNA, which runs at about 1500 bp, was cut from the gel, and the DNA extracted. The cDNA concentrations were determined spectrophotometrically, and the microgram value was converted to copy number using standard methods (e.g., a software program which converts weight to copy number, such as that described in U.S. Provisional Patent Application 61/161,568).

1 μg of cDNA was serially diluted ($1:10^2$, $1:10^3$, $1:10^4$, $1:10^5$, $1:10^6$, and $1:10^7$) to generate the standard curve using the real time PCR setting with generic primers (SEQ ID NOs: 11 and 12) as crossing point values. Each point on the standard curve was averaged from triplicate determinations. Exact mRNA copy numbers of the patient samples were determined by running the cDNA sample in triplicates and averaged. The average crossing points of the sample were read from the standard curve generated by the real time PCR, and the copy number was determined.

Based on the mRNA copy numbers in SDHB/SDHD tumors, the metastatic state of 9 tumors was assigned in a blinded analysis (see Table 3).

TABLE 3

Determination of CPE-ΔN mRNA
copy number in SDHB/D tumors.

| Sample Number | State[1] | Geno-type | Copy Number | Follow-up (years of follow-up or time to recurrence/metastasis) |
|---|---|---|---|---|
| S55 | Benign[2] | SDHD | 167,550 | Disease free[4] (4 yrs) |
| S85 | Benign[2] | SDHD | 187,809 | Disease free (2 yrs) |
| S73 | Benign[3] | SDHB | 200,000 | Disease free (2.5 yrs) |
| S82 | Benign[3] | SDHB | 200,714 | Disease free (2.4 yrs) |
| S31 | Benign | SDHB | 11,894,562 | Metastatic (2 yrs) |
| S18 | Metastatic | SDHB | 5,583,686 | Metastatic |
| S22 | Metastatic | SDHB | 10,937,462 | Metastatic |
| S95-A-1 | Metastatic | SDHB | 6,181,873 | Metastatic |
| M20 | Metastatic | SDHB | 11,057,100 | Metastatic |

[1]Diagnosis at the time of surgery
[2]Benign adrenal
[3]Benign extra-adrenal
[4]Disease free refers to no clinical symptoms or signs of disease with negative imaging and biochemical data.

Four of the SDHB patients diagnosed with metastatic tumors based on the pathology of the tumor and lymph node invasion had copy numbers within the range of 5-11 million copies.

In the group of three SDHB patients diagnosed with benign tumors, two had copy numbers of about 200,000. Interestingly, one of these patients had a copy number of almost 12 million. This patient was recalled, and it was found that he had developed recurrence and metastasis.

The two SDHD patients with benign tumors showed CPE-ΔN mRNA copy numbers of about 180,000.

Patients with CPE-ΔN mRNA copy numbers of 180,000-200,000 that had tumors diagnosed as benign showed no recurrence between 2-5 years after surgery.

These analyses demonstrate the accuracy (100%) of this method of assaying CPE-ΔN biomarker in diagnosing and predicting future metastasis in SDHB/SDHD patients.

To further test the method, a group of MEN2 patients were examined in a blinded study. Most MEN2 patients develop bilateral adrenal tumors. Extra-adrenal localization and malignant disease are very rare in this group of patients. Four MEN2 patients were diagnosed with benign tumors at the time of surgery (see Table 4). Of those, three had CPE-ΔN mRNA copy numbers in the 170,000-200,000 range consistent with the numbers found in SDHD/B with benign tumors. Two patients had copy numbers of 6.7-14.8 million. The patients showed symptoms of recurrence.

TABLE 4

Determination of CPE-ΔN mRNA copy number in MEN2 tumors.

| Sample Number | State[1] | Geno-type | Copy Number | Follow-up (years of follow-up or time to recurrence/metastasis) |
|---|---|---|---|---|
| M05 | Benign[2] | MEN2 | 14,825,680 | Recurrent (8 yrs) |
| M06 | Recurrent[3] | MEN2 | 6,750,151 | Recurrent (4 yrs) |
| M12 | Benign[2] | MEN2 | 194,801 | Disease free[4] (6.5 yrs) |
| M13 | Benign[2] | MEN2 | 190,139 | Disease free (6 yrs) |
| M15 | Benign[2] | MEN2 | 168,984 | No information |

[1]Diagnosis at the time of surgery
[2]Benign adrenal
[3]Recurrent in contralateral adrenal surgical bed
[4]Disease free refers to no clinical symptoms or signs of disease with negative imaging and biochemical data.

A group of eight patients with PHEO/PGL that had no hereditary basis for the disease also were studied. This group has been termed "sporadic" cases. Of the eight cases diagnosed as having a benign tumor at time of surgery, four of them had CPE-ΔN mRNA copy numbers in the 130,000-185,000 range and have not shown any recurrence 2-5 years post surgery (Table 5).

In contrast, there were four patients that had CPE-ΔN mRNA copy numbers of 4.3-7.2 million. One patient has since developed thyroid cancer, and another showed capsular and vascular invasion, indicating that the primary tumors of these patients were not typical benign tumors. Another patient had an unusually large (8 cm) adrenal tumor, while one had surgery only a year ago, and it is too early to know if he will show recurrence later. Nevertheless, the high CPE-ΔN mRNA copy number in these patients certainly warrants close follow-up.

TABLE 5

Determination of CPE-ΔN mRNA copy number in sporadic PHEO/PGL tumors.

| Sample Number | State[1] | Geno-type | Copy Number | Follow-up |
|---|---|---|---|---|
| S39 | Benign | SPORADIC | 175,080 | |
| S45 | Benign | SPORADIC | 6,181,873 | Thyroid cancer |
| S48 | Benign | SPORADIC | 184,761 | |
| S49 | Benign | SPORADIC | 181,713 | |
| S67 | Benign | SPORADIC | 135,279 | |
| S71 | Benign | SPORADIC | 6,451,057 | Large tumor (8 cm) |
| S75 | Benign | SPORADIC | 4,357,402 | |
| S76 | Benign | SPORADIC | 7,228,701 | Capsular and vascular invasion |

[1]At the time of surgery

These results from 22 patients in different categories (SDHB/D, MEN2, and sporadic) clearly demonstrate that the measurement of CPE-ΔN mRNA copy numbers can be used as a prognostic tool in diagnosing and predicting recurrence/metastasis of PHEOs/PGLs. Tumors with CPE-ΔN mRNA copy numbers of less than 200,000 clearly are benign. In contrast, tumors with CPE-ΔN mRNA copy numbers of 1-12 million or greater are malignant, or patients with these tumors have a high probability of showing recurrence and future metastasis.

EXAMPLE 3

This example demonstrates that the expression level of CPE-ΔN is correlated with metastasis.

Differentiated thyroid carcinoma (DTC) is a malignancy of epithelial origin that is on the rise in the U.S. The vast majority of patients who have low risk disease do not develop distant metastases and have excellent survival. However, the minority of patients who have high-risk disease develop distant metastases and experience reduced survival.

Some prognostic indicators are helpful in predicting which patients are more likely to develop distant metastases. Examples of prognostic indicators that can be assessed at the time of thyroidectomy are age at diagnosis, tumor size, and soft tissue invasion. Other prognostic indicators include BRAF mutations, cyclin D expression, galectin-3 expression, p53 expression, tumor vascularity, post-operative serum thyroglobulin levels, and the presence of variant types of differentiated thyroid cancer such as the tall cell variant. However, the performance of these prognostic indicators is imperfect. Distant metastases clearly portend a worse prognosis, but the presence of such disease frequently is not discovered until imaging studies are performed at various follow-up visits after the initial thyroidectomy.

An area of particular interest with respect to thyroid cancer prognosis is potential gender differences. Differentiated thyroid cancer has a higher incidence and prevalence in females than males. There is disagreement as to whether there is truly a different biologic behavior of thyroid carcinoma between genders, or whether thyroid cancer is simply detected at a later, less treatment-responsive stage in males. Certainly the role of estrogen as a modulator of apoptosis in thyroid cancer cells has been investigated, but although the findings from such studies could potentially explain the increased incidence of thyroid cancer in women, the findings do not provide on explanation for the better prognosis of thyroid cancer in females.

There is, therefore, a need for an accurate prognostic indicator that can be readily assessed at the time of initial surgery.

The use of CPE-ΔN mRNA copy number as biomarker for metastasis for DTC was evaluated in a blinded study. The CPE-ΔN mRNA copy numbers from resected DTC from different categories (papillary carcinoma and hurthle cell carcinoma) were determined using the methods described in Example 2 (see Table 6).

TABLE 6

Determination of CPE-ΔN mRNA copy number in DTC tumors.

| Sample Number | State* | Description | Copy Number | Follow-up |
|---|---|---|---|---|
| 12-T | Metastasis | Papillary Carcinoma | 11,097,674 | Died from the cancer |
| 39-T | Metastasis | Papillary Carcinoma | 14,279,070 | |
| 39N | Normal | Surrounding non tumor tissue | 3,260 | |
| 219-T-2 | No Metastasis | Papillary Carcinoma | 563,118 | |
| 219-N-1 | Normal | Surrounding non tumor tissue | 162,888 | |
| 296T-1 | No Metastasis | Papillary Carcinoma | 235,311 | No recurrence after 2 yrs |
| 296N-2 | Normal | Surrounding non tumor tissue | 6,530 | |
| 189T | No Metastasis | Papillary Carcinoma | 6,114 | |
| 189-N-1 | Normal | Surrounding non tumor tissue | 7,950 | |
| 333T | No Metastasis | Papillary Carcinoma | 7,025 | |
| 650T-1 | No Metastasis | Hurthle cell carcinoma | 223,347 | |
| 246-1-T | No Metastasis | Hurthle cell carcinoma | 602,598 | |

*At the time of surgery

CPE-ΔN mRNA copy numbers of metastatic tumors from two patients were 11 million and 14 million (see Table 6). CPE-ΔN mRNA copy numbers in tumors that did not show metastasis ranged from 6,000-600,000. Where there was patient follow up data available, the patient with 11 million copies died of the cancer, whereas a patient with 235,000 copies did not show recurrence in 2 years.

From the eight patient samples for DTC, it can be concluded that CPE-ΔN mRNA copy numbers of 250,000 or less fall into a very low risk group with values typically found in normal tissue and benign tumors. This is similar to PGLs (see Example 2).

In contrast, CPE-ΔN mRNA copy numbers of greater than 1 million indicates a metastatic tumor. Patients having non-malignant tumors with CPE-ΔN mRNA copy numbers between 400,000-1 million (e.g., 500,000, 600,000, 700,000, 800,000, 900,000, or ranges of the values described herein) could potentially develop recurrence or metastasis and should be carefully monitored.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A cDNA consisting of a nucleic acid sequence that only encodes the amino acid sequence of SEQ ID NO: 2.
2. A cDNA consisting of the nucleic acid sequence of SEQ ID NO: 1.
3. A vector comprising a nucleic acid consisting of a nucleic acid sequence that only encodes the amino acid sequence of SEQ ID NO: 2.
4. A vector comprising a nucleic acid consisting of the nucleic acid sequence of SEQ ID NO: 1.
5. A composition comprising the cDNA of claim 1.
6. A composition comprising the cDNA of claim 2.
7. The vector of claim 3, wherein the vector is a recombinant plasmid or viral vector.
8. The vector of claim 4, wherein the vector is a recombinant plasmid or viral vector.

* * * * *